US009320677B2

(12) United States Patent
Johnson et al.

(10) Patent No.: US 9,320,677 B2
(45) Date of Patent: *Apr. 26, 2016

(54) DEFIBRILLATOR DISPLAY INCLUDING CPR DEPTH INFORMATION

(71) Applicant: ZOLL Medical Corporation, Chelmsford, MA (US)

(72) Inventors: Guy R. Johnson, Gloucester, MA (US); Annemarie Silver, Bedford, MA (US); Gary A. Freeman, Newton Center, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/231,944

(22) Filed: Apr. 1, 2014

(65) Prior Publication Data

US 2014/0213941 A1    Jul. 31, 2014

Related U.S. Application Data

(63) Continuation of application No. 13/208,871, filed on Aug. 12, 2011, now Pat. No. 8,725,253, which is a continuation-in-part of application No. 13/025,348, filed on Feb. 11, 2011, now Pat. No. 8,880,166.

(60) Provisional application No. 61/304,119, filed on Feb. 12, 2010, provisional application No. 61/307,690, filed on Feb. 24, 2010.

(51) Int. Cl.
*A61N 1/00*   (2006.01)
*A61H 31/00*  (2006.01)
(Continued)

(52) U.S. Cl.
CPC ............... *A61H 31/00* (2013.01); *A61H 31/005* (2013.01); *A61N 1/3925* (2013.01);
(Continued)

(58) Field of Classification Search
CPC ......... A61N 1/08; A61N 1/39; A61N 1/3993; A61N 2001/08; A61N 1/3925; A61H 31/00; A61H 31/005
USPC ......................................................... 607/5, 7
See application file for complete search history.

(56) References Cited

U.S. PATENT DOCUMENTS 4,198,963 A    4/1980   Barkalow et al.
4,326,507 A    4/1982   Barkalow
(Continued)

FOREIGN PATENT DOCUMENTS

EP    1595575    11/2005
EP    1834622     9/2007
(Continued)

OTHER PUBLICATIONS

Chinese Office Action, with English translation, CN Application No. 201180009391.8, mailed Mar. 14, 2014, 17 pages.
(Continued)

*Primary Examiner* — Theodore Stigell
*Assistant Examiner* — Michael Carey
(74) *Attorney, Agent, or Firm* — The Webb Law Firm

(57) ABSTRACT

Systems and methods related to the field of cardiac resuscitation, and in particular to devices for assisting rescuers in performing cardio-pulmonary resuscitation (CPR) are described herein. In some aspects, a system and method can include obtaining values for depths of a plurality of the chest compressions and information about a physiological parameter of the person and providing periodic feedback to a user about chest compressions performed by the user based at least in part on the values for the depths of the plurality of the chest compressions and a target compression depth.

23 Claims, 22 Drawing Sheets

(51) Int. Cl.
*A61N 1/39* (2006.01)
*G06F 19/00* (2011.01)
*G09B 19/00* (2006.01)

(52) U.S. Cl.
CPC ......... *A61N 1/3993* (2013.01); *G06F 19/3406* (2013.01); *G06F 19/3481* (2013.01); *G09B 19/003* (2013.01); *A61H 2201/1253* (2013.01); *A61H 2201/5007* (2013.01); *A61H 2201/5043* (2013.01); *A61H 2201/5084* (2013.01); *A61H 2230/04* (2013.01); *A61H 2230/045* (2013.01); *A61H 2230/207* (2013.01); *A61H 2230/30* (2013.01)

(56) References Cited

U.S. PATENT DOCUMENTS

| | | | |
|---|---|---|---|
| 4,397,306 | A | 8/1983 | Weisfeldt et al. |
| 5,020,516 | A | 6/1991 | Biondi et al. |
| 5,377,671 | A | 1/1995 | Biondi et al. |
| 5,490,820 | A | 2/1996 | Schock et al. |
| 5,957,856 | A | 9/1999 | Weil et al. |
| 6,179,793 | B1 | 1/2001 | Rothman et al. |
| 6,213,960 | B1 | 4/2001 | Sherman et al. |
| 6,269,267 | B1 | 7/2001 | Bardy et al. |
| 6,312,399 | B1 | 11/2001 | Lurie et al. |
| 6,390,996 | B1 | 5/2002 | Halperin et al. |
| 6,807,442 | B1 | 10/2004 | Myklebust et al. |
| 7,118,542 | B2 | 10/2006 | Palazzolo et al. |
| 7,220,235 | B2* | 5/2007 | Geheb et al. ............ 601/41 |
| 7,242,979 | B1 | 7/2007 | Kelly et al. |
| 7,272,441 | B1 | 9/2007 | Chapman et al. |
| 7,565,194 | B2 | 7/2009 | Tan et al. |
| 7,650,181 | B2 | 1/2010 | Freeman et al. |
| 7,774,060 | B2 | 8/2010 | Westenskow et al. |
| 7,993,290 | B2 | 8/2011 | Lund et al. |
| 8,105,249 | B2 | 1/2012 | Freeman |
| 8,204,589 | B2 | 6/2012 | Freeman |
| 8,321,011 | B2 | 11/2012 | Parascandola et al. |
| 8,478,401 | B2 | 7/2013 | Freeman |
| 8,725,253 | B2* | 5/2014 | Johnson ............ A61N 1/3925 607/5 |
| 8,880,166 | B2 | 11/2014 | Tan et al. |
| 2002/0133197 | A1 | 9/2002 | Snyder et al. |
| 2003/0144699 | A1 | 7/2003 | Freeman |
| 2004/0039419 | A1 | 2/2004 | Stickney et al. |
| 2004/0082888 | A1* | 4/2004 | Palazzolo et al. ............ 601/41 |
| 2004/0215112 | A1 | 10/2004 | Mollenauer et al. |
| 2004/0230140 | A1 | 11/2004 | Steen |
| 2004/0267325 | A1 | 12/2004 | Geheb et al. |
| 2005/0085799 | A1 | 4/2005 | Luria et al. |
| 2005/0101889 | A1 | 5/2005 | Freeman et al. |
| 2005/0256415 | A1 | 11/2005 | Tan et al. |
| 2006/0058848 | A1 | 3/2006 | Piraino et al. |
| 2006/0089574 | A1 | 4/2006 | Paradis |
| 2006/0129191 | A1 | 6/2006 | Sullivan et al. |
| 2006/0173501 | A1 | 8/2006 | Stickney et al. |
| 2006/0270952 | A1 | 11/2006 | Freeman et al. |
| 2007/0060785 | A1 | 3/2007 | Freeman et al. |
| 2007/0213775 | A1* | 9/2007 | Snyder ............ 607/7 |
| 2007/0219588 | A1 | 9/2007 | Freeman |
| 2008/0015645 | A1 | 1/2008 | Kelly et al. |
| 2008/0027338 | A1 | 1/2008 | Lu et al. |
| 2009/0024175 | A1 | 1/2009 | Freeman |
| 2009/0054743 | A1 | 2/2009 | Stewart |
| 2010/0049266 | A1 | 2/2010 | Ochs et al. |
| 2010/0211127 | A1 | 8/2010 | Eerden |
| 2010/0222718 | A1 | 9/2010 | Freeman et al. |
| 2011/0040217 | A1 | 2/2011 | Centen |
| 2011/0082510 | A1 | 4/2011 | Sullivan |
| 2011/0117529 | A1 | 5/2011 | Barash et al. |
| 2011/0172550 | A1 | 7/2011 | Martin et al. |
| 2011/0202100 | A1 | 8/2011 | Tan et al. |
| 2011/0202101 | A1 | 8/2011 | Tan et al. |

FOREIGN PATENT DOCUMENTS

| | | |
|---|---|---|
| JP | 200546609 A | 2/2005 |
| JP | 2005515009 A | 5/2005 |
| JP | 2005-339533 | 12/2005 |
| JP | 2006503659 A | 2/2006 |
| JP | 2007512043 A | 5/2007 |
| JP | 2009507609 A | 2/2009 |
| WO | WO 96/28129 | 9/1996 |
| WO | WO 02/072197 | 9/2002 |
| WO | WO 2004/058351 | 7/2004 |
| WO | WO 2005/043303 | 5/2005 |
| WO | WO 2005/043306 | 5/2005 |
| WO | WO 2006/104977 | 10/2006 |
| WO | 2009037621 A2 | 3/2009 |

OTHER PUBLICATIONS

Aase et al., "CPR Artifact Removal from Human ECG Using Optimal Mutlichannel Filtering," IEEE Transactions on Biomedical Engineering 47(11):1440-1449 (2000).

Authorized officer Eva San Miguel, International Search Report and Written Opinion in PCT/US2011/024464 mailed May 24, 2011, 14 pages.

Authorized officer Sara Bertoni, International Search Report and Written Opinion in PCT/US2011/024507, mailed Aug. 4, 2011, 12 pages.

Authorized officer Lee W. Young, International Search Report and Written Opinion in PCT/US2012/49904, mailed Oct. 22, 2012, 12 pages.

Barash et al., "Novel Technology to Limit Chest Compression Interruption with Experienced Advanced Life Support Providers," American Heart Association Abstract P65, Circulation 2009, 120:S1455.

Li et al., "Identifying potentially shockable rhythms without interrupting cardiopulmonary resuscitation," Critical Care Medicine 36(1):198-203 (2008).

Lloyd et al., "Hands-On Defibrillation. An Analysis of Electrical Current Flow Through Rescuers in Direct Contact With Patients During Biphasic External Defibrillation," Journal of the American Heart Association Circulation 117:2510-2514 (2008).

Povoas and Bisera, "Electrocardiographic waveform analysis for predicting the success of defibrillation", Crit Care Med (2000) 28(11):210-211.

Povoas et al., "Predicting the success of defibrillation by electrocardiographic analysis," Resuscitation 53:77-82 (2002).

Robertson et al., "Defibrillator Charging During On-Going Chest Compressions: A Multi-Center Study of In-Hospital Resuscitation," American Heart Association Abstract 2644, Circulation 2009, 120(18)2:S670.

Ruiz de Gauna et al., "A method to remove CPR artifacts from human ECG using only the recorded ECG," Resuscitation 76:271-278 (2008).

Silver et al., "A New Defibrillator Mode Reduces Chest Compression Interruptions for Lay Rescuers and BLS Providers," American Heart Association Abstract P173, Circulation 2009, 120:S1479.

Sullivan et al., "How Much Can Hands-off Time Be Reduced by Performing Rhythm Analysis During CPR?" American Heart Association Abstract P176, Circulation 2009, 120:S1479.

Young et al., "Amplitude spectrum area: Measuring the probability of successful defibrillation as applied to human data", Crit Care Med (2004) 32(9):356-358.

Yu et al., "The resuscitation blanket: A useful tool for "hands-on" defibrillation," Resuscitation 81:230-235 (2010).

Japanese Office Action, with English translation, JP Application No. 2012-553017, mailed Oct. 28, 2014, 10 pages.

Extended European Search Report, Application No. 12824042.1, mailed Nov. 24, 2014, 8 pages.

American Heart Association, "Highlights of the 2010 American Heart Association Guidelines for CPR and ECC", 2010, pp. 1-28.

* cited by examiner

DEFIBRILLATOR DISPLAY INCLUDING CPR DEPTH INFORMATION

CROSS-REFERENCE TO RELATED APPLICATION

This application is a continuation of and claims priority under 35 U.S.C. §120 to U.S. patent application Ser. No. 13/208,871, now U.S. Pat. No. 8,725,253, entitled "DEFIBRILLATOR DISPLAY INCLUDING CPR DEPTH INFORMATION," filed on Aug. 12, 2011, which is a continuation-in-part of application U.S. patent application Ser. No. 13/025,348, entitled "DEFIBRILLATOR DISPLAY," filed on Feb. 11, 2011, now published as U.S. Publication No. 2011/0202100, which claims benefit of priority to U.S. Provisional Application Ser. No. 61/304,119, filed on Feb. 12, 2010, entitled "DEFIBRILLATOR CHARGING," and U.S. Provisional Application Ser. No. 61/307,690, filed on Feb. 24, 2010, entitled "DEFIBRILLATOR DISPLAY," the entire contents of each of which are hereby incorporated by reference.

TECHNICAL FIELD

This document relates to cardiac resuscitation and in particular to systems and techniques for assisting rescuers in performing cardio-pulmonary resuscitation (CPR).

BACKGROUND

The heart relies on an organized sequence of electrical impulses to beat effectively. Deviations from this normal sequence are known as "arrhythmia." Certain medical devices include signal processing software that analyzes electrocardiography (ECG) signals acquired from a medical patient (e.g., a victim at a scene of an emergency) to determine when a cardiac arrhythmia such as ventricular fibrillation (VF) or shockable ventricular tachycardia (VT) exists. These devices include automated external defibrillators (AEDs), ECG rhythm classifiers, and ventricular arrhythmia detectors. An AED is a defibrillator—a device that delivers controlled electrical shock to a patient—while being relatively easy to use, such as by providing verbal prompts to a provider of care to "talk" the provider through a process of evaluating a patient for, attaching the patient to, and activating, AED therapy. Certain of the medical devices just discussed are also capable of recognizing the two distinct cardiac waveforms: VT and VF.

VT is a tachydysrhythmia that originates from a ventricular ectopic focus, characterized by a rate that is typically greater than 120 beats per minute and wide QRS complexes. VT may be monomorphic (typically regular rhythm originating from a single focus with identical QRS complexes) or polymorphic (unstable, may be irregular rhythm, with varying QRS complexes). An example rhythm for an unstable VT is illustrated in FIG. 1A. Depending on the rate and the length of time that the VT has been sustained, a heart in the VT state may or may not produce a pulse (i.e., pulsatile movement of blood through the circulatory system). The cardiac activity in the VT state still has some sense of organization (note that the "loops" are all basically the same size and shape). If there is no pulse associated with this VT rhythm, then the VT is considered to be unstable and a life threatening condition. An unstable VT can be treated with an electrical shock or defibrillation.

Supraventricular tachycardia (SVT) is a rapid heartbeat that begins above the heart's lower chambers (the ventricles). SVT is an abnormally fast heart rhythm that begins in one of the upper chambers of the heart (atria), a component of the heart's electrical conduction system called the atrioventricular (AV) node, or both. Although SVT is rarely life-threatening, its symptoms, which include a feeling of a racing heart, fluttering or pounding in the chest or extra heartbeats (palpitations), or dizziness can be uncomfortable.

VF is usually an immediate life threat. VF is a pulseless arrhythmia with irregular and chaotic electrical activity and ventricular contraction in which the heart immediately loses its ability to function as a pump. VF is the primary cause of sudden cardiac death (SCD). An example rhythm for VF is illustrated in FIG. 1B. This waveform does not have a pulse associated with it. There is no organization to this rhythm (note the irregular size and shape of the loops). The pumping part of the heart is quivering like a bag of worms, and it is highly unlikely that this activity will move any blood. The corrective action for this rhythm is to defibrillate the heart using an electrical charge.

A normal heart beat wave starts at the sinoatrial node (SA node) and progresses toward the far lower corner of the left ventricle. A massive electrical shock to the heart can correct the VF and unstable VT rhythms. This massive electrical shock can force all the cardiac cells in the heart to depolarize at the same time. Subsequently, all of the cardiac cells go into a short resting period. The hope is that the sinoatrial node (SA node) will recover from this shock before any of the other cells, and that the resulting rhythm will be a pulse-producing rhythm, if not normal sinus rhythm.

Many AEDs implement algorithms to recognize the VT and VF waveforms by performing ECG analyses at specific times during a rescue event of a patient using defibrillation and cardio-pulmonary resuscitation (CPR). The first ECG analysis is usually initiated within a few seconds after the defibrillation electrodes are attached to the patient. Subsequent ECG analyses may or may not be initiated, based upon the results of the first analysis. Typically, if the first analysis detects a shockable rhythm, the rescuer is advised to deliver a defibrillation shock. Following the shock delivery, a second analysis can be initiated automatically to determine whether the defibrillation treatment was successful or not (i.e., the shockable ECG rhythm has been converted to a normal or other non-shockable rhythm). If this second analysis detects the continuing presence of a shockable arrhythmia, the AED advises the user to deliver a second defibrillation treatment. A third ECG analysis may then be executed to determine whether the second shock was or was not effective. If a shockable rhythm persists, the rescuer is then advised to deliver a third defibrillation treatment.

Following the third defibrillator shock or when any of the analyses described above detects a non-shockable rhythm, treatment protocols recommended by the American Heart Association and European Resuscitation Council require the rescuer to check the patient's pulse or to evaluate the patient for signs of circulation. If no pulse or signs of circulation are present, the rescuer can be directed to perform CPR on the victim for a period of one or more minutes. The CPR includes rescue breathing and chest compressions. Following this period of CPR, the AED reinitiates a series of up to three additional ECG analyses interspersed with appropriate defibrillation treatments as described above. The sequence of three ECG analyses/defibrillation shocks followed by 1-3 minutes of CPR, continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

Many studies have reported that the temporary discontinuation or excessive pausing of precordial compression can significantly reduce the recovery rate of spontaneous circulation and 24-hour survival rate for victims. Thus, it is useful to recognize abnormal heart rhythms during chest compressions. There is recent clinical evidence showing that performing chest compressions before defibrillating the patient under some circumstances can be beneficial. Specifically, it is clinically beneficial to treat a patient with chest compressions before defibrillation if the response times of the medical emergency system result in a delay of more than four minutes, such that the patient is in cardiac arrest for more than four minutes. Chest compression artifact rejection can employ spectral analysis of the ECG, defibrillation success prediction, and therapeutic decision-making typically specify a set of parameters in the ECG frequency spectrum to be detected. For example, U.S. Pat. No. 5,683,424 compares a centroid or a median frequency or a peak power frequency from a calculated frequency spectrum of the ECG to thresholds to determine if a defibrillating shock is necessary.

Unfortunately, existing AEDs require batteries able to deliver large amounts of current due to the charging requirements of defibrillator high voltage capacitors. This results in batteries that are excessive in both size and weight that limit both their portability, convenience, and in the case of external, wearable defibrillators such as the LifeVest (ZOLL Medical, Chelmsford, Mass.) their wearability and comfort. In addition, batteries continue to be the least reliable element of the AEDs currently manufactured, with regular recalls resulting from manufacturing defects as well as normal end-of-life degradation that always occurs with batteries, but are particularly troublesome for life-saving equipment.

SUMMARY

This document describes systems and techniques that may be used to provide information about patient status and/or CPR administration during administration of CPR to a patient. The systems and techniques described herein aim to identify the most important data and to display the information in an efficient and effective manner to a rescuer. The data displayed to the rescuer can include information about the quality of the CPR administered by the rescuer, including, for example, CPR chest compression depth. The data displayed to the rescuer can also include information about the patient status. The data about the patient and CPR is presented graphically and/or textually in a manner that improves the ability of a rescuer to quickly understand the state of a patient and to make clinical decisions that will benefit the patient.

This document describes systems and techniques for automatically determining a target chest compression depth based on measured physiological parameters of a patient. In some examples, the target compression depth can be provided to a rescuer as a guide for administration of chest compressions and the system can modify the target compression depth by a fraction of an inch.

In certain implementations, such systems and technique may provide one or more advantages. For example, patient care may be improved when a rescuer can easily view well-formatted information in a single location. Also, rescuers may be able to modify their administration of CPR (e.g., modify the compression depth) to be more effective because the system has determined whether a different depth is likely to be more effective based on measured parameters and presented relevant data to the rescuer in an understandable manner.

In one implementation, a method for providing adaptive Cardiopulmonary Resuscitation (CPR) treatment to a person in need of emergency assistance includes obtaining, by a portable computing unit, values for depths of a plurality of the chest compressions. The method also includes obtaining, by the portable computing unit, information about a physiological parameter of the person. The method also includes providing, at a first rate, periodic feedback to a user about chest compressions performed by the user based at least in part on the values for the depths of the plurality of the chest compressions and a target compression depth, and periodically determining, at a second rate that is slower than the first rate, whether to adjust the target compression depth based at least in part on the information about the physiological parameter of the person, so that multiple instances of feedback about chest compressions performed by the user are provided to the user for each instance of determining whether to adjust the target compression depth.

Embodiments can include one or more of the following.

The method can include providing information about a target CPR compression depth to the user.

The periodic feedback to a user about chest compressions performed by the user can include feedback to the user about the compression depth.

Providing the periodic feedback to the user about chest compressions can include displaying on a graphical display screen of a defibrillator, an indication of the values for the depths of one or more of the plurality of the chest compressions and an indication of the target compression depth.

Providing the periodic feedback to the user about chest compressions can include displaying on a graphical display screen of a defibrillator, a graphical representation of the depths of one or more of the plurality of the chest compressions and an indication of the target compression depth.

Providing the periodic feedback to the user about chest compressions can include displaying on a graphical display screen of a defibrillator, a graph having a visual indicia representing the target compression depth and visual indicia representing the values for the depths of one or more of the plurality of the chest compression displayed above or below the visual indicia representing the target compression depth.

Providing the periodic feedback to the user about chest compressions can include displaying on a graphical display screen of a defibrillator, a graph having a bar representing the target compression depth and additional bars representing depths of one or more of the plurality of chest compressions.

Compressions that are deeper than the target compression depth can be displayed below the bar representing the target compression depth and compressions that are more shallow than the target compression depth can be displayed above the bar representing the target compression depth.

Providing the periodic feedback to a user about chest compressions can include displaying an icon that indicates whether the chest compressions are being performed properly.

The method can also include receiving information about the patient's heart activity and displaying on a graphical display, with the feedback about chest compressions, an electrocardiogram of the patient.

Displaying the electrocardiogram can include moving an electrocardiogram trace laterally across the display.

The periodic feedback to the user about chest compressions can include a bar graph that displays the depth of the plurality of the chest compressions and an indicator of the target compression depth.

Lengths of bars in the bar graph can represent compression depths.

Obtaining information regarding depths of a plurality of the chest compressions can include obtaining data regarding chest compressions performed on the patient comprises from an accelerometer that is positioned to move in coordination with the patient's breastbone.

The portable computing unit can be integrated with a portable defibrillator.

The portable computing unit can be a touchscreen tablet computer.

The method can also include displaying a graphical representation of the information about the physiological parameter of the person.

The method can also include displaying a graphical representation of the information about the physiological parameter including a time varying graph of the physiological parameter.

The method can also include displaying a graphical representation of the information about the physiological parameter including trend data associated with a trend in values of the physiological parameter.

The method can also include determining a trend in the obtained information about the physiological parameter of the person and displaying a graphical representation of the determined trend.

Displaying the graphical representation of the determined trend can include providing multiple arrows showing potential trend directions and providing a visual indicia associated with one of the multiple arrows, the visual indicia being indicative of a direction of the determined trend.

The first rate can be a per compression rate and the second rate can be a time period of between 10 seconds and one minute.

The first rate can be a rate of 5 seconds or less and the second rate can be a rate of 10 seconds or greater.

In some additional aspects, an external defibrillator includes one or more sensors arranged to contact a patient and obtain measurements regarding chest compressions performed on the patient. The defibrillator also includes one or more additional sensors arranged to contact a patient and obtain measurements regarding a physiological parameter of the patient. The defibrillator also includes a video display screen for displaying, at a first rate, periodic feedback to a user about chest compressions performed by the user based at least in part in the values for the depths of the plurality of the chest compressions and a target compression depth. The defibrillator also includes a processor connected to memory that stores computer instructions for periodically determining, at a second rate that is slower than the first rate, whether to adjust the target compression depth based at least in part on the information about the physiological parameter of the person, so that multiple instances of feedback about chest compressions performed by the user are provided to the user for each instance of determining whether to adjust the target compression depth.

Other features and advantages will be apparent from the description and drawings, and from the claims.

DETAILED DESCRIPTION

This description discusses systems and techniques for providing defibrillation energy in a controlled manner. In general, such energy needs to be built up, such as by charging a capacitor, and that build up of energy may take an appreciable length of time. Using the techniques discussed here, a system can analyze a patient's needs in advance of the time to delivery defibrillation pulse (e.g., while a rescuer is performing chest compressions) and can begin charging a capacitor or other appropriate energy delivery mechanism sufficiently in advance of the time that a shock will be needed, so that the shock can be delivered as soon as it is needed.

Figures 2, 2A:
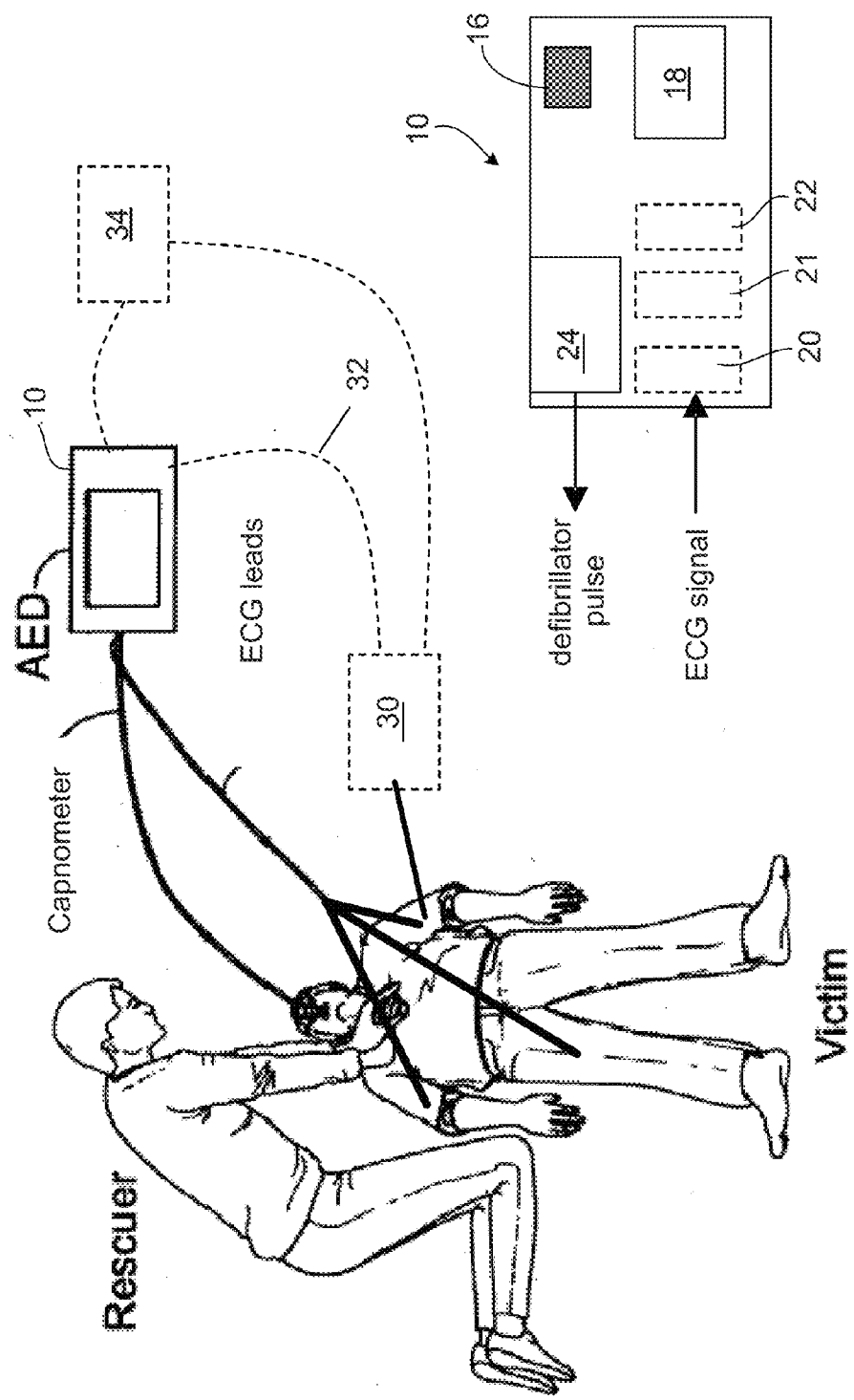
FIG. 2 is a diagram of one implementation including an automatic electronic defibrillator (AED) and a multiple lead electrocardiograph (ECG) device.
FIG. 2A is a diagram of the AED of FIG. 2.

Referring now to FIG. 2, an AED 10 is shown that may be used to provide a defibrillation shock at an appropriate time. In the figure, which shows an example implementation, a rescuer uses an AED 10 to automatically monitor a victim during cardiac resuscitation. The AED 10 uses measured ECG signals to monitor the victim's heart, and charges the defibrillation device within the AED while the victim is resuscitated using chest compressions techniques. In some examples, the manner in which the defibrillation device is charged (e.g., the rate of charge, the total amount of charge stored) can be based on the measured ECG signals. Advantageously, charging the defibrillation device during CPR chest compressions reduces the amount of time that the victim is not receiving chest compressions because, if a shockable rhythm exists, the device is armed and ready to deliver the shock as soon as the rescuer completes the chest compressions.

The AED 10 includes a speaker 16, a display screen 18, an analog-to-digital converter 20, a processor 22, and a defibrillator pulse generator 24. The analog-to-digital converter 20 is connected to a set of ECG leads that are in turn attached to the victim. The ECG leads pass signals to the processor 22 for monitoring the electrical rhythms of the victim's heart. The converter 20 sends the signals from the ECG leads to the processor 22. The processor 22 monitors the victim's heart for dangerous rhythms using the ECG signals while the victim is resuscitated using chest compressions techniques.

If the AED 10 detects a dangerous heart rhythm, the AED 10 generates an alarm signal. The alarm signal is noticeable to the rescuer. The AED 10 can generate a defibrillating shock to the victim when the rescuer issues a command to the AED 10 directing such a shock. The defibrillating shock is intended to remedy the dangerous rhythm of the victim's heart.

The AED 10 also includes a charging module 19 that is configured to charge the AED during chest compressions. The module 19 can adaptively charge the AED based on monitored ECG signals. In some examples, the defibrillator is pre-charged only if a shockable rhythm is likely to exist as determined by analysis of the monitored ECG signals. In some additional examples, the level of charge for the device is determined and set based on the monitored ECG signals. In some additional examples, the method of charging (e.g., the rate of charge) varies based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer.

The AED 10 uses a rhythm advisory method for a) quantifying the frequency-domain features of the ECG signals; b) differentiating normal and abnormal ECG rhythms, such as VF; c) detecting the onset of abnormal ECG rhythms; and d) making decisions about the physiological states of the heart. This frequency-domain measure can be reliable with or without the presence of the chest compression artifact in the ECG signals. The AED 10, after identifying the current physiological state of the heart, can make a decision about appropriate therapeutic action for the rescuer to make and communicate the action to the rescuer using the speaker 16 and the display screen 18.

The AED 10 may incorporate functionality for performing additional therapeutic actions such as chest compressions, ventilations, or delivery of intravenous solution-containing metabolic or constitutive nutrients. Based on the results of the analysis of the rhythm advisory method, the AED 10 may automatically deliver the appropriate therapy to the patient.

The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some examples, one or more therapeutic delivery devices 30 automatically deliver the appropriate therapy to the patient. The therapeutic delivery devices 30 can be, for example, a portable chest compression device, a drug infusion device, a ventilator and/or a device that includes multiple therapies such as defibrillation, chest compression, ventilation and drug infusion. The therapeutic delivery devices 30 are physically separate from the defibrillator AED 10, and control of the therapeutic delivery devices 30 may be accomplished by a communications link 32. The communications link 32 may take the form of a cable but preferably the link 32 is via a wireless protocol.

In other examples, control and coordination for the overall resuscitation event and the delivery of the various therapies may be accomplished by a device 34 or processing element that is external to the AED 10. For instance, the device 34 may download and process the ECG data from the AED 10; analyze the ECG signals, perform relevant determinations like those discussed above and below based on the analysis, and control the other therapeutic devices 30, including the AED 10. In other examples, the AED 10 may perform all the processing of the ECG, including analyzing the ECG signals, and may transmit to the control device 34 only the final determination of the appropriate therapy, whereupon the control device 34 would perform the control actions on the other linked devices 30.

Chest compression artifacts can be separated from the ECG signal components, making it possible for the AED 10 to process the ECG signal without halting the processing during chest compressions. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety.

It has been recognized that good chest compressions during CPR is essential to saving more victims of cardiac arrest. The compression rate recommended by the American Heart Association in its guidelines is greater than 100 compressions per minute. Many studies have reported that the discontinuation of chest compressions, such as is commonly done for ECG analysis and charging of a defibrillator, can significantly reduce the recovery rate of spontaneous circulation and 24-hour survival rate. Because of safety issues with delivery of a high voltage defibrillation shocks with voltages of 1000-2000 volts, rescuers are taught to cease chest compressions and remove their hands from the victim's chest before initiating the defibrillation shock. By analyzing ECG signals during chest compressions as a mechanism to permit earlier charging of an energy delivery device (e.g., a capacitor) in a defibrillator device, the gaps in providing chest compressions can be reduced, and patient care increased.

Figure 3A:
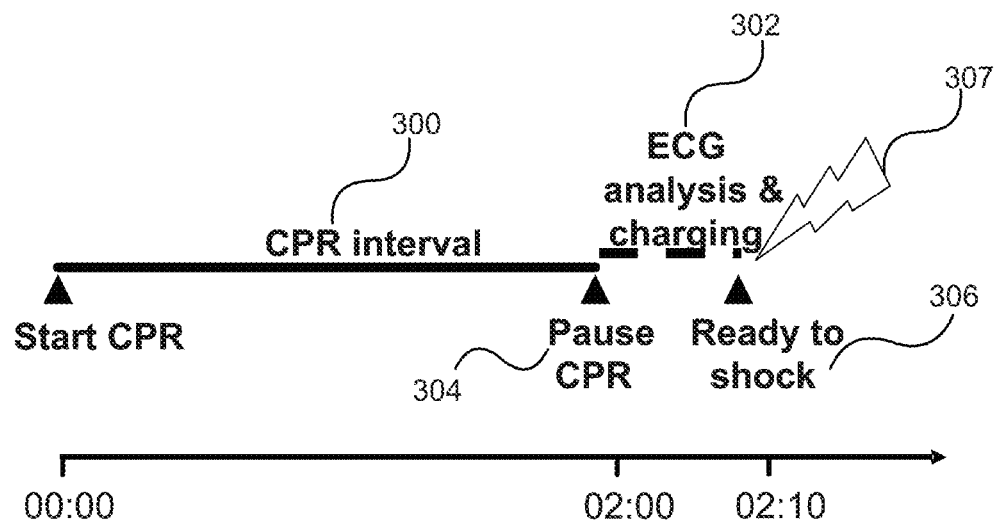
FIGS. 3A and 3B are examples of ECG analysis and charging cycles.

FIG. 3A shows an example of an ECG analysis and charging cycle in which charging of a defibrillator device starts after a CPR interval has ended. As shown in the figure, in operation of some AED devices, the rescuer is instructed to perform chest compressions for a two minute CPR interval 300 after which the rescuer is instructed to pause his or her performance of CPR 304. At this point, the rescuer removes his or her hands from the victim, ECG analysis is performed, and the defibrillator device is charged (interval 302). As such, a time period elapses (time period 302) during which the rescuer is not delivering chest compressions to the victim. This elapsed time period before delivery of the shock 307 can be, for example, about 10 seconds—of which a portion is devoted to performing the ECG analysis and a portion is devoted to charging the defibrillation device. While methods exist for processing ECG signals without halting the processing during CPR chest compressions, a time period may still elapse between the cessation of chest compressions and availability of an adequate charge for delivering a shock.

Figure 3B:
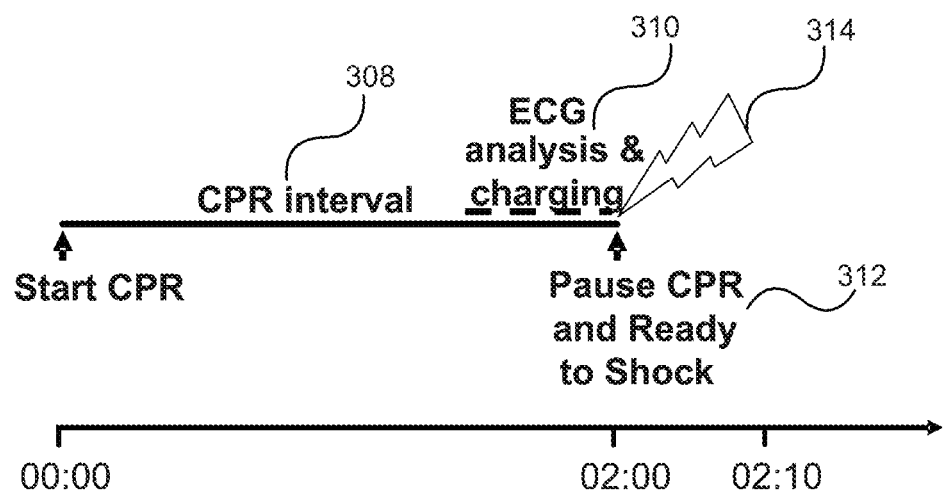

FIG. 3B shows an example of an ECG analysis and charging cycle in which charging of a defibrillator device starts before a CPR interval has ended. The CPR interval can be based on a length of time of administration of chest compressions (e.g., as shown in FIG. 3B), a total number of chest compressions, a total number of effective chest compressions based on depth or rate of the compression, a total length of time of effective chest compressions, or can be variable based on one or more observed factors such as the ECG analysis and/or the timing of interventions such as drug delivery. The CPR interval can additionally be updated by software or firmware to handle different CPR protocols such that the device is charged and the defibrillation therapy is delivered according to the protocol. As shown in the figure, in operation methods described herein, the defibrillation device is charged while the rescuer is providing the CPR chest compressions. Similar to the method described with respect to FIG. 3A, the rescuer is instructed to perform chest compressions for a two minute CPR interval 308. During the two minute CPR interval, ECG analysis is performed and the defibrillator device is charged (interval 310). After the CPR interval is complete, the rescuer is instructed to pause CPR 312, and shock 314 can be delivered almost immediately to the victim because the defibrillator device has already had time to charge. Because the defibrillator device is fully charged before the rescuer ceases chest compressions, the time period during which the rescuer is not delivering chest compressions to the victim can be greatly reduced and the shock can be delivered immediately or almost immediately after chest compressions are completed. For example, the elapsed time between the end of the CPR interval and the delivery of the shock (if a shockable rhythm exists) can be less than about 5 seconds (e.g., less than about 5 seconds, less than about 3 seconds, less than about 2 seconds, less than about 1 second, less than about ½ a second). In some embodiments, the length of time between the rescuer ceasing chest compressions and delivery of the shock can be simply based on the amount of time the rescuer spends locating and pressing a button on the AED device that causes the AED device to deliver the shock to the victim.

In some additional embodiments, the AED device may utilize a brief period of time (e.g., while the rescuer locates and presses the button) after the rescuer ceases chest compressions to reconfirm the desirability of delivering the shock to the victim. For example, a rescuer can be instructed to visually inspect and confirm that a shockable rhythm exists and/or the AED device can continue to collect and analyze ECG signals (in the absence of chest compressions resulting in less artifacts in the ECG signal) to re-confirm the desirability of delivering the shock. In some additional examples, the AED device can alert the rescuer of a presumed, observed underlying rhythm during the administration of chest compressions and potentially additionally provide a confidence indication that provides an indication how confident the system is in analysis and determination of the underlying rhythm. Providing such information can aid the rescuer in performing a reconfirmation of the desirability of delivering the shock. In general, a time period for re-confirmation based on analysis of an ECG signal without chest compression artifacts can be brief (e.g., less than about 5 seconds, less than about 3 seconds, less than about 2 seconds). The time period for re-confirmation can be based on physiological characteristics (e.g., heart rate that is fast or slow) and/or a desired confidence level for the ECG analysis.

Because of safety issues with charging the defibrillation device to a voltage of 1000-2000 volts while the rescuer is in contact with the victim, safety interlocks can be included in a defibrillator device to ensure that the voltage is not discharged before the rescuer removes his or her hands from the victim. The defibrillator safety interlocks can include one or more software-controlled-hardware and/or software mechanisms that prevent the defibrillator from accidentally discharging outside of the unit. In order for the defibrillator to deliver a shock, the AED device confirms that a variety of software and hardware states are met during the charging process. Once the defibrillator reaches a full level of charge, a therapy button is enabled. Enabling the therapy button removes a final hardware safety interlock and selects the output for the therapy charge to the patient connector instead of the internal resistor network used to dissipate charge when a shock is not delivered. Once enabled, a rescuer presses the therapy button and the AED registers the press which closes a therapy delivery relay and delivers the defibrillation pulse. The safety interlocks control the enablement of the therapy button and a do not allow the rescuer to deliver a shock to the victim until other actions occur that disable the safety interlocks.

In some additional methods, an electrically insulating protection layer extends over the surface of the patient so that manual compressions may continue safely and unabated during the charging of the defibrillation device and delivery of the defibrillation shock. An exemplary electrically insulating protection layer is described, for example, in U.S. Pat. No. 6,360,125, which is incorporated by reference herein in its entirety.

In some embodiments, the period for administration of chest compressions is not preset, rather the period can be variable based on the observed EGC signals. ECG analysis may start while CPR chest compressions are being administered. When the AED device determines that a shockable rhythm exists based on the ECG signals or otherwise makes a determination that the appropriate therapy would be to deliver the defibrillation shock, the AED device can begin charging. In some additional examples, in addition to detecting shockable rhythm, the device may also determine the coarseness of the VF (e.g., AMSA) and adjust the interval in order to shock at the highest AMSA. CPR chest compressions continue while the device is charging. The AED device can optionally instruct the rescuer of an amount of time that he/she should continue to administer chest compressions based on the length of time used to charge the defibrillator device. Once the device is fully charged, the rescuer can be instructed to pause chest compressions and the shock can be delivered almost immediately to the victim.

Figure 4A:
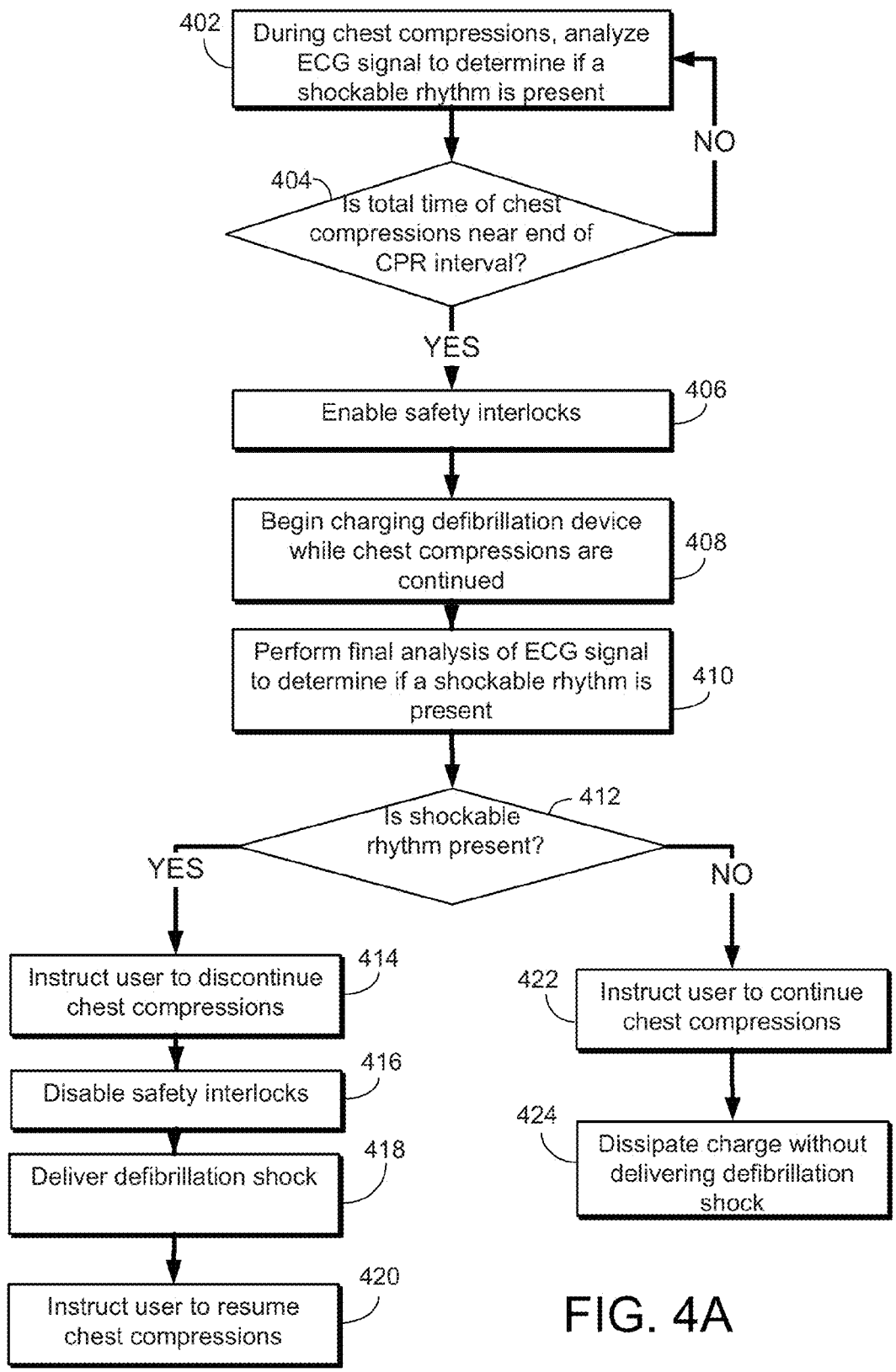
FIG. 4A is a flow chart showing actions taken to charge a defibrillation device during chest compressions associated with a CPR interval.

FIG. 4A is a flow chart showing actions taken to charge a defibrillation device during chest compressions associated with a CPR interval. As noted above, charging the defibrillation device in addition to analyzing an ECG signal during chest compressions can provide the advantage of reducing the amount of time that a rescuer is not administering chest compressions to the victim. In general, an interval (e.g., a set length of time) is set for the administration of chest compressions. During this interval, the system analyzes an ECG signal and charges the defibrillation device. Safety interlocks are enabled that prevent accidental dissipation of the charge in the defibrillation device during the CPR chest compression interval. At the end of the CPR interval, a decision of whether to shock the victim is made based on the ECG signal analysis, and the stored charge is either administered to the victim or dissipated internally. In some additional examples, rather than dissipating the charge internally when the system determines that a shockable rhythm is not present at the end of the CPR interval, the system can store the charge for potential delivery in a subsequent CPR interval.

The example process here begins at box 402, where the AED analyzes an ECG signal to determine if a shockable rhythm is present in the victim. The ECG signal is measured while chest compressions are being administered to the victim. As such, the AED separates the chest compression artifact from the ECG signal components to process the ECG signal without halting the processing during CPR chest compressions (e.g., as described in U.S. Pat. No. 7,565,194).

At box 404, the AED determines if the current time is near the end of the CPR interval (e.g., within about 10-30 seconds of the end of the CPR interval). Exemplary CPR intervals can be between 0 and 5 minutes (e.g., 30 seconds, 1 minute, 2 minutes, 3 minutes, 4 minutes, and 5 minutes). If the current time within a determined window for performing chest compressions is not near the end of the CPR interval, the AED device continues to analyze the ECG signals (box 402). If the current time is near the end of the CPR interval, the AED enables safety interlocks at box 406 (though the interlocks may be enabled even before this time).

As the chest compressions continue, the AED begins charging the defibrillation device at box 408 with the safety interlocks enabled. The amount of time needed to charge the defibrillation device can vary based on the current used to charge the device and the total amount of charge desired. As such, the system begins charging the defibrillation device in advance of the end of the CPR interval such that the defibrillation device will be fully charged at the end of the CPR interval. For example, a window for performing CPR can be determined when the CPR cycle begins, a time for charging the defibrillation device can be looked up or otherwise determined, and the system may be programmed to check, at a time in advance of the end of the window that substantially corresponds to the charging time, for whether a shockable rhythm is present At box 410, the AED performs a final analysis of the ECG signal to determine if a shockable rhythm is present in the victim. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety. If a shockable rhythm is not observed, at box 422, the AED instructs the rescuer to continue chest compressions. Thus, if a shockable rhythm does not exist, the victim receives uninterrupted chest compressions. Such chest compressions may not place the heart back into normal operation, but they may nonetheless maximize perfusion of blood through the heart until a more highly-trained rescuer can arrive and take over.

At box 424, the AED dissipates the charge from the defibrillation device without delivering a shock to the victim. For example, the AED can dissipate the stored charge using a resistor network inside the AED device such that the charge can be dissipated without requiring the rescuer to discontinue chest compressions. The dissipation may occur by dumping the charge, for example. The charge may also be "recycled" back into a battery on the device so as to extend the battery life.

If a shockable rhythm is observed, at box 414, the AED device instructs the rescuer to discontinue chest compressions. For example, the AED device can provide audible instructions to the rescuer via a speaker and/or can provide a visual instruction to the rescuer via a display device. At box 416, the AED disables the safety interlocks, thus making it possible for the shock to be delivered through electrodes that are attached to the victim.

At box 418, the AED device delivers the defibrillation shock to the victim. Such delivery may occur in response to the rescuer pressing a button on the AED to provide a command to deliver the shock. The shock may also be delivered automatically, such as after the AED voices a command to stand clear of the victim. The shock is delivered without significant delay after the cessation of chest compressions because the device has been previously pre-charged while the chest compressions were being administered.

At box 420, the AED device instructs the user to resume chest compressions. This initiates another CPR cycle during which a similar ECG analysis will be performed. The process just described may thus be repeated until a shock succeeds in placing the victim's heart roughly back into a normal operating mode, or until additional caregivers arrive to attempt different resuscitation approaches.

In some embodiments, a reconfirmation of the desirability to deliver the defibrillation shock to the victim is performed after the rescuer ceases chest compressions. Because the re-confirmation is performed when the rescuer is not delivering chest compressions, the ECG signals analyzed by the AED device during the reconfirmation are expected to be less noisy and have less artifacts because artifacts from the chest compressions are no longer present. As such, an ECG analysis may have higher degree of confidence. In general, as described above, a time period for re-confirmation based on analysis of an ECG signal without chest compression artifacts can be brief (e.g., less than about 5 seconds, less than about 3 seconds, less than about 2 seconds).

In some embodiments, the AED device can determine whether to perform a reconfirmation analysis based on one or more factors associated with the prior EGC analysis such as a certainty value. For example, if the prior EGC analysis results in a high certainty that delivering the defibrillation shock to the victim is the appropriate therapy (e.g., a high certainty of conversion to a perfusing rhythm) then the AED may deliver the shock nearly immediately after the rescuer ceases chest compressions (e.g. without a reconfirmation period). On the other hand, if the prior EGC analysis has a lower certainty that delivering the defibrillation shock to the victim is the appropriate therapy then the AED may perform a reconfirmation analysis before making a final determination of whether to deliver the defibrillation shock. Additionally or alternatively a determination of whether to perform a reconfirmation analysis can be based on a confidence value associated with the level of confidence that the EGC signal analysis is correct. For example, if the signal is extremely noisy and has a large presence of artifacts, the confidence of the analysis may be lower making it desirable to reconfirm the analysis in the absence of the chest compressions.

Figure 4B:
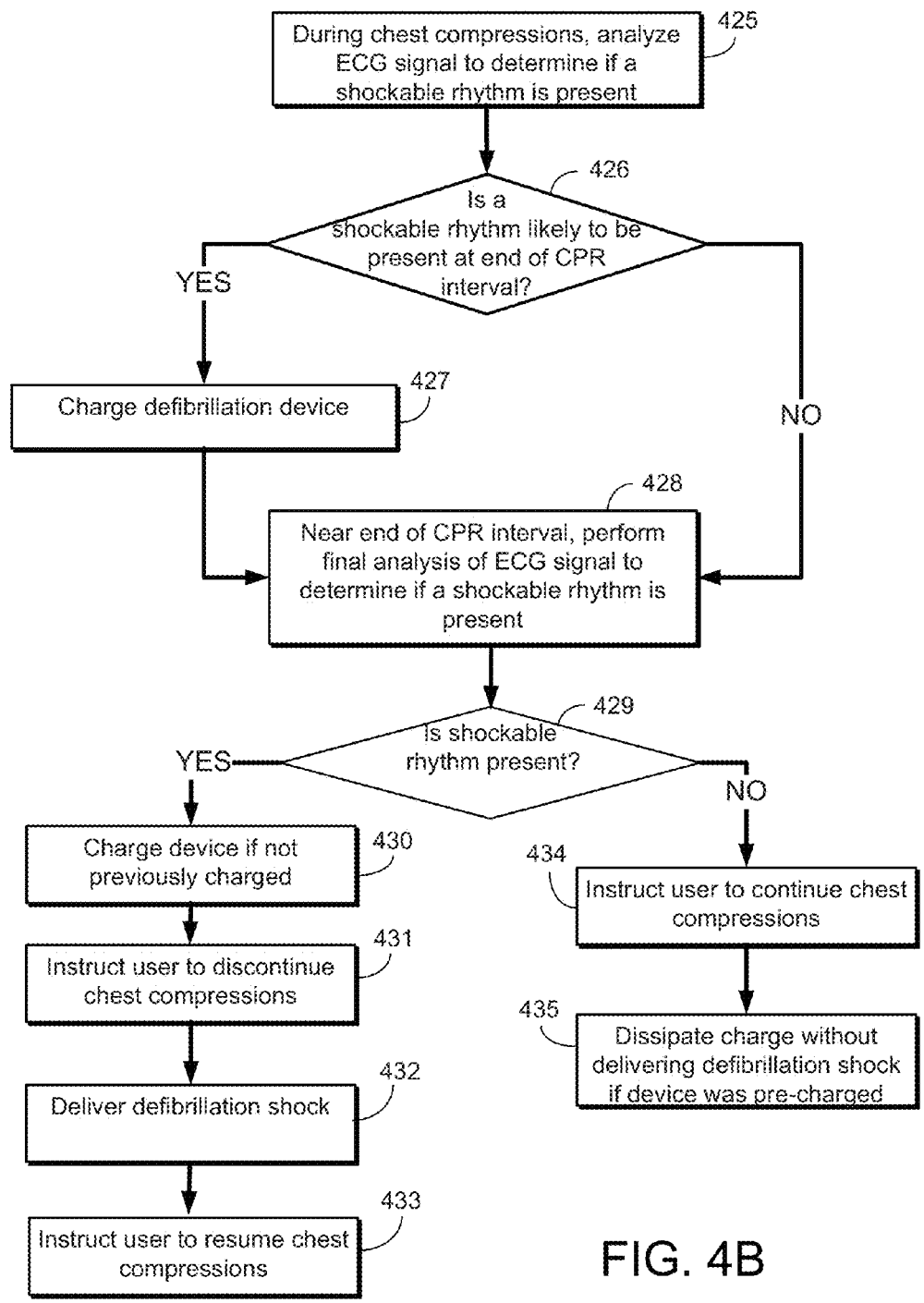
FIG. 4B is a flow chart showing actions taken to charge a defibrillation device using different current levels that are selected based on the likelihood of a shockable rhythm being observed.

FIG. 4B is a flow chart showing actions taken to charge a defibrillation device using different current levels that are selected based on the likelihood of a shockable rhythm being observed. Portable AED devices may be powered by a battery or other power supply having a limited lifetime. In order to conserve power for future uses of the AED device or for the administration of multiple shocks to a single victim, various charging algorithms can be used. In some examples, an AED device makes a determination of whether a shockable rhythm exists in the victim and only charges the defibrillator device if a shockable rhythm exists. Such a charging algorithm conserves power because if a shockable rhythm is not observed, the AED device does not charge the defibrillator and then dump or dissipate the charge.

The example process begins at box 425, where the AED analyzes an ECG signal while chest compressions are being administered to a victim to determine if a shockable rhythm is likely to be present in the victim at the end of the CPR interval (e.g., as described in U.S. Pat. No. 7,565,194). At box 426, the AED determines if a shockable rhythm is likely to be present in the victim at the end of the CPR interval. While the CPR interval will continue regardless of the outcome of the analysis, the determination is used to decide whether to begin charging the defibrillator device. The time at which to make such a determination may be set by a determination of how long it will take to charge the defibrillator device. When different possible rates of charge are available to the system, and maximum time charge can be set for the ECG analysis, a rate of charge may be determined, and then the actual charging may begin at a time preceding the end of CPR that is substantially the amount of time the charge will take at the computed rate of charge.

A threshold for determining whether to pre-charge the defibrillator can be different from a threshold used to determine whether to administer a shock to the victim. For example, because the determination is used to decide whether to pre-charge the AED device, a lower threshold may be used such that the device will be fully charged at the end of the CPR interval if a shock may be administered. For example, an accuracy measure can be used to set the thresholds. For example, an observed signal resulting in a high accuracy value (e.g., a confidence of greater than about 90%) can be used as to set a threshold for determining whether to administer a defibrillation shock to the victim while a lower confidence (e.g., a confidence of 50% or greater) can be used to set a threshold for determining whether to begin charging the defibrillation device. For example, an AMSA number that is associated with a certain accuracy level in predicting a successful conversion can be used to set the thresholds for deciding whether to pre-charge the defibrillator, the rate of charging the defibrillator, and whether to administer the defibrillation shock. This AMSA number can be customized based on a request of the rescuer or the medical director. For example, an AMSA number that is associated with a accuracy level of 90% or greater (e.g., 90% or 95%) in predicting a successful conversion can be used to set the threshold for administering a defibrillation shock and an AMSA number that is associated with a accuracy level of 70% or greater (e.g., 70%, 80%, 90%) in predicting a successful conversion can be used to set the threshold for deciding whether to pre-charge the defibrillator. In other examples, an AMSA number that is associated with an accuracy level of 70% or greater (e.g., 70%, 80%, 90%) in predicting a successful conversion can be associated with the fastest possible rate in charging the defibrillator; The lower value the AMSA number is, the rate of charging is set to (e.g., half speed in charging when an AMSA number associated with an accuracy level of 50% is observed). In some embodiments, other predictors of conversion success (e.g., SCE) can be used.

If a shockable rhythm is not likely to be present in the victim at the end of the CPR interval, the AED continues to receive and analyze the ECG signals. At box 428 near the end of the CPR cycle, the AED device performs a final analysis of the ECG signal to determine whether a shockable rhythm exists. This second determination of whether a shockable rhythm exists serves as a confirmation that a shockable rhythm still does not exist, so that a rescuer does not forego providing a shock to the victim in a situation where the patient's condition has changed in a manner that would make a shock would be beneficial.

In contrast, if the system determines that a shockable rhythm is likely to exist, at box 427, the AED pre-charges the defibrillation device. This charging occurs while the rescuer is administering the CPR chest compressions. At box 428 near the end of the CPR cycle, the AED device performs a final analysis of the ECG signal.

At box 429, the AED device determines whether a shockable rhythm exists. This second determination of whether a shockable rhythm exists serves as a confirmation that a shockable rhythm still exists, so that a rescuer is not led to give a shock to a patient when the patient's condition has changed in a manner that would make the shock essentially futile. A different threshold can be used for the determination of whether to administer the shock to the victim than was used to determine whether to pre-charge the defibrillator.

If a shockable rhythm does not exist at this later time and under this later standard (though the standard may also be the same for deciding whether to pre-charge and deciding whether to remove the safety interlocks and allow the shock actually to be delivered), the AED instructs the rescuer to continue chest compressions at box 434 such that the victim receives uninterrupted chest compressions. At box 435, the AED dissipates the charge (e.g., using one or more of the methods described herein) from the defibrillation device without delivering a shock to the victim if the device was pre-charged (e.g., at box 427).

If a shockable rhythm is observed, at box 430, the AED device determines whether the defibrillator was pre-charged (e.g., at box 427) and charges the defibrillator if it was not previously pre-charged (or completes any still-incomplete charging). At box 431, the AED device instructs the rescuer to discontinue chest compressions (e.g., using one or more of the methods described herein). At box 432, the AED device delivers the shock and at box 432, the AED device instructs the user to resume chest compressions. This initiates another CPR cycle during which a similar ECG analysis will be performed.

Figure 4C:
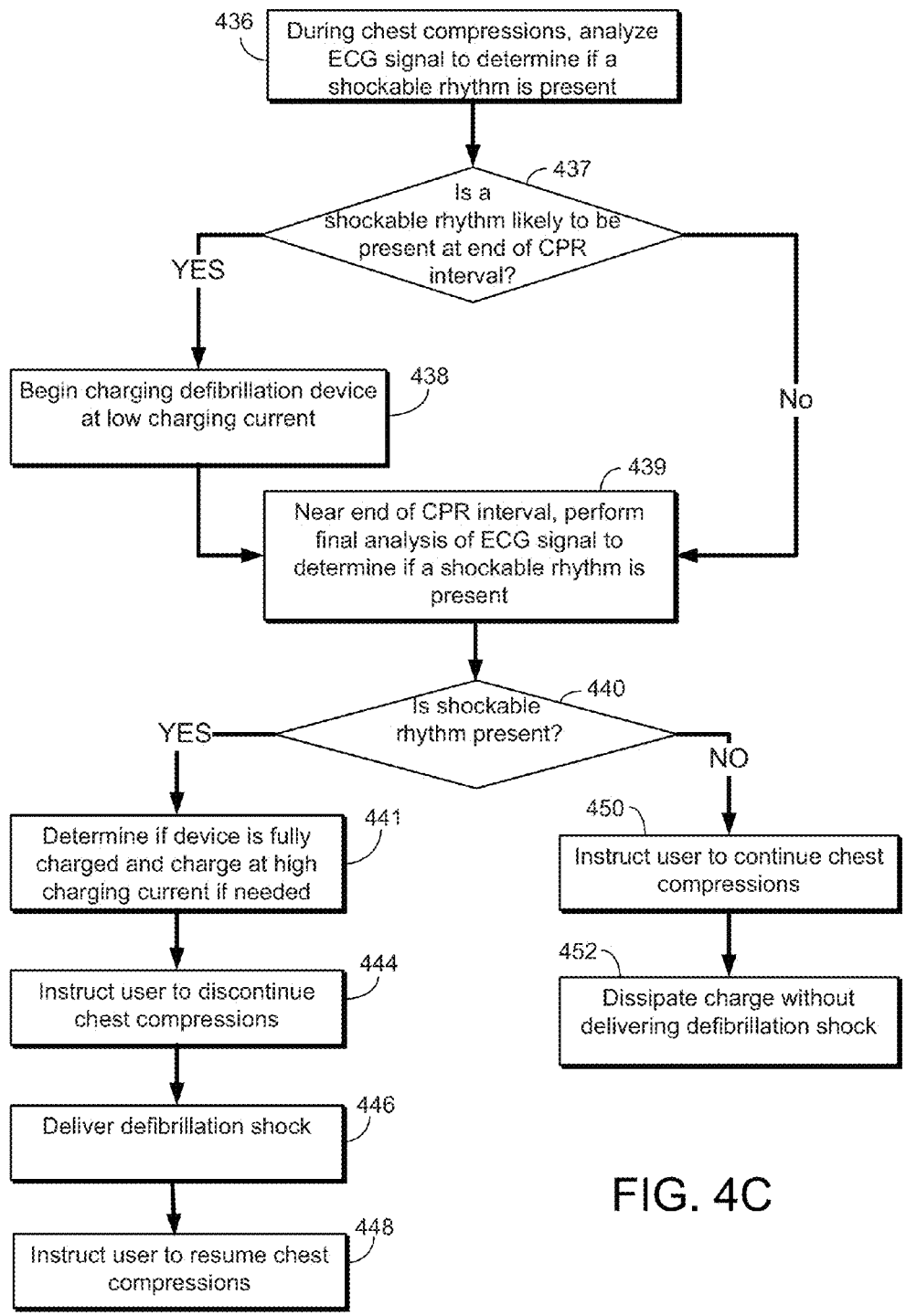
FIG. 4C is a flow chart showing actions taken to adaptively charge a defibrillation device using different current levels based on the likelihood of a shockable rhythm being observed.

FIG. 4C is a flow chart showing actions taken to charge a defibrillation device using different current levels based on the likelihood of a shockable rhythm being observed. One exemplary way to conserve power in an AED is to charge the AED device at a lower current over a longer period of time (e.g., over a period of at least 30 seconds), resulting in less of a drain on the batter power as compared to charging the AED device to the same total charge using a higher current and a shorter period of time (e.g., over a period of at most 10 seconds). A percentage calculated by dividing the lower charging current by the higher charging current can be greater than about 50% (e.g., greater than about 50%, greater than about 60%, greater than about 75%) and less than about 90% (e.g., less than about 90%, less than about 80%). Additionally, in some examples to conserve power in the AED, the AED can store the charge from a previous cycle where a shock was not delivered to the victim and in subsequent charging cycles, a smaller amount of charge is needed to "top off" the charge to the fully charged level.

Charging the AED device over a longer period of time at a lower current can occur during the CPR interval because the typical CPR interval is between 2-5 minutes. Both charging the device at a lower current (that is selected to permit full or substantially full charging during the available charging interval before a shock may be needed) and/or only charging the device if it is likely that a shock will be administered to the victim can contribute to an extended battery life for the AED device. Drawing less total current from the battery can provide additional advantages such as enabling the use of a smaller battery (and thereby enabling a smaller and lighter AED) and/or enabling the use of alternative power devices such as solar power and/or human generated power.

In some additional examples, the speed of charging can be adjusted based upon battery life. For example, if there is wall power the AED could be quickly charged every time, if the device relies on solar power with strong charge the AED could be charged using a slower charging cycle, if the AED is powered by solar power with low power the AED could be charged using a very slow charging cycle. Additionally, the CPR interval could be increased if power is limited so there is sufficient time for charging.

In one embodiment, a "crank" generator may be employed. Since the time available to charge the defibrillator capacitor can be increased to as much as 3-10 minutes using the systems and methods described herein, a 200 joule capacitor only requires at most approximately a 1.5 watt power source, assuming a 3 minute charge duration and a high voltage flyback circuitry efficiency of 75%. Due to leakage of a typical film capacitor at maximum voltage of approximately 2 Watts, a generator of 2.5-3 Watts would be required. Such a power supply may be an external hand crank power supply available commercially (SuperBattery with Crank Generator, Teledex, Inc., N.J.), or a built-in crank generator in the defibrillator with a power output sufficient to charge the defibrillator capacitor in the allotted time. As part of the generator, an additional energy storage element will preferably be included, for instance a battery as contained in the Superbattery described above, or a so-called "ultracapacitor", such as that manufactured by Maxwell Technologies (San Diego), for instance the 350 Farad, part number BCAP0350 E270 T11. The ultracapacitor is used to maintain power for the low-voltage circuitry such as signal amplifiers and digital processing circuitry when the rescuer has stopped providing mechanical energy to the generator. The mechanical energy for the generator may alternatively be contained in a structure positioned on the patient's sternum, which will be compressed during cardiopulmonary resuscitation. Currently, devices exist commercially (CPR-STATPADZ, ZOLL Medical, Chelmsford, Mass.) which measure the performance of the rescuer doing chest compressions by measuring the compression depth via an accelerometer sensor within a low-profile housing positioned under the rescuers hands while they are compressing the patient's sternum during CPR. The housing may additionally be constructed to flexibly deform during sternal compressions, thus causing motion of the actuator of a generator, for instance a linear motion electric power generator as described in U.S. Pat. No. 5,818,132. A typical patient requires approximately 100 pounds of force to depress the sternum to the required depth of 2 inches, as per the American Heart Association recommendations. Thus, by allowing for a deformation of the housing of 0.5-1 inches would increase the compression depth of the rescuer to 2.5-3 inches to achieve the same sternal depth of 2 inches, but would provide the requisite 2.5-3 Watts of necessary power, assuming a generator efficiency of 40%. Alternatively, the housing may be a spring-loaded two piece housing with accelerometer and generator contained within the housing, the upper portion of the generator actuator affixed to the upper portion of the housing, the generator and the lower portion of the actuator affixed to the lower housing, and power generated when the spacing between the upper and lower housings is changed.

In another embodiment, the lid of the AED might be surfaced with a solar cell, thus providing approximately 100 square inches of available surface area. Standard, commercially available amorphous Silicon crystal cells currently provide approximately 45 milliwatts per inch squared. This power can be doubled by employing a more expensive crystalline cell as well as alternative structures. Thus, the solar cell would be able to provide 4-10 Watts of power, which is more than sufficient for the systems and methods described herein. As with the human powered generator approach, an electrical energy storage element would be included, such as an ultracapacitor, in addition to the defibrillator capacitor, for powering the analog and digital low-voltage electronics, if for instance a shadow from the rescuer passes in front of the solar cells during device use. Thus, even with batteries that have failed or whose performance has degraded to the point that they are unable to power the defibrillator, it is now possible to have a backup power source for use in emergencies, not currently available with existing technology. In the preferred embodiment, a fail-safe switch, relay or transistor would be employed that would disconnect the failed batteries from the electronics, so that power would not be diverted from the generator or solar cell by the batteries during operation.

Because the defibrillator capacitor can be charged over a significantly increased period of time, the peak charging current is significantly decreased by a factor of ten or more. This allows for significantly smaller batteries to be used to power the defibrillator. In general, the batteries can include one or more primary cells and/or one or more secondary (e.g., rechargeable) cells. Examples of significantly smaller batteries that can be used to power the defibrillator include any battery (or combination of multiple batteries) with a relatively low power output of, for example, less than about 10 W (e.g., less than about 10 W, less than about 7 W, less than about 5 W, less than about 4 W, less than about 3 W). In some examples, the power output can be greater than about 2.5 W and less than 10 W (e.g., between about 2.5 W and about 10 W, between about 2.5 W and about 7 W, between about 2.5 W and about 5 W, between about 2.5 W and about 4 W, between about 2.5 W and about 3 W). In one particular example, the current ZOLL AEDPlus requires ten lithium CR123 commercial batteries to power the defibrillator, at a significant size, weight and cost expense. With the systems and methods described herein, this can be reduced to 1, or at most, 2 CR123 batteries. In addition, it is now possible to use even smaller alkaline batteries, such as a standard commercially-available 'C' size alkaline cell.

At box 436, while chest compressions are being administered, the AED analyzes an ECG signal (e.g., as described in U.S. Pat. No. 7,565,194) and at box 437, the AED determines if a shockable rhythm is likely to be present in the victim at the end of the CPR interval. While the CPR interval will continue regardless of the outcome of the analysis, the determination is used to decide whether to begin charging the defibrillator device.

If a shockable rhythm is not likely to be present in the victim at the end of the CPR interval, the AED continues to receive and analyze the ECG signals. At box 439, near the end of the CPR cycle, the AED performs a final analysis of the ECG signal to determine whether a shockable rhythm exists. The analysis may also continue until a shockable rhythm is present.

In contrast, if the system determines that a shockable rhythm is likely to exist (either initially or upon further monitoring and analysis), at box 438, the AED device begins pre-charging the defibrillation device at a low charging current. In other examples, the charging current can be based on the length of time remaining in the CPR interval. For example, a charging current can be selected such that the device will be fully charged at the end of the CPR interval. This may result in the charging occurring at a low rate over an extended period of time (e.g., over a period of time greater than about 30 seconds, over a period of time greater than about 45 seconds, over a period of time greater than about 1 minute). For example, if a shockable rhythm is determined initially, the charging rate may be relatively low, whereas if there was no initial shockable rhythm but the device senses a shockable rhythm later in the chest compression cycle, the charging rate may be relatively fast. This charging occurs while the rescuer is administering the CPR chest compressions (though some may occur after the end of the provision of CPR chest compressions, though not enough that it would create a substantial effect on the timing of the CPR).

At box 439 near the end of the CPR cycle, the AED device performs a final analysis of the ECG signal, and at box 440, the AED device determines whether a shockable rhythm exists. If a shockable rhythm does not exist, the AED instructs the rescuer to continue chest compressions at box 450 such that the victim receives uninterrupted chest compressions. At box 452, the AED dissipates the charge (e.g., using one or more of the methods described herein) from the defibrillation device without delivering a shock to the victim if the device was pre-charged (e.g., at box 438).

If a shockable rhythm is observed, at box 441, the AED device determines whether the defibrillator has reached a full level of charge and charges the defibrillator to the full level of charge (if needed) at a high current. For example, while the pre-charging can occur at a low current over an extended period of time, charging to reach the full charge if the device is not fully charged in time (or charging if not pre-charged) can occur at a high current and during as short of period as is practical.

At box 444, the AED device instructs the rescuer to discontinue chest compressions (e.g., using one or more of the methods described herein). At box 446, the AED device delivers the shock and at box 448, the AED device instructs the user to resume chest compressions. This initiates another CPR cycle during which a similar ECG analysis will be performed.

Figure 4D:
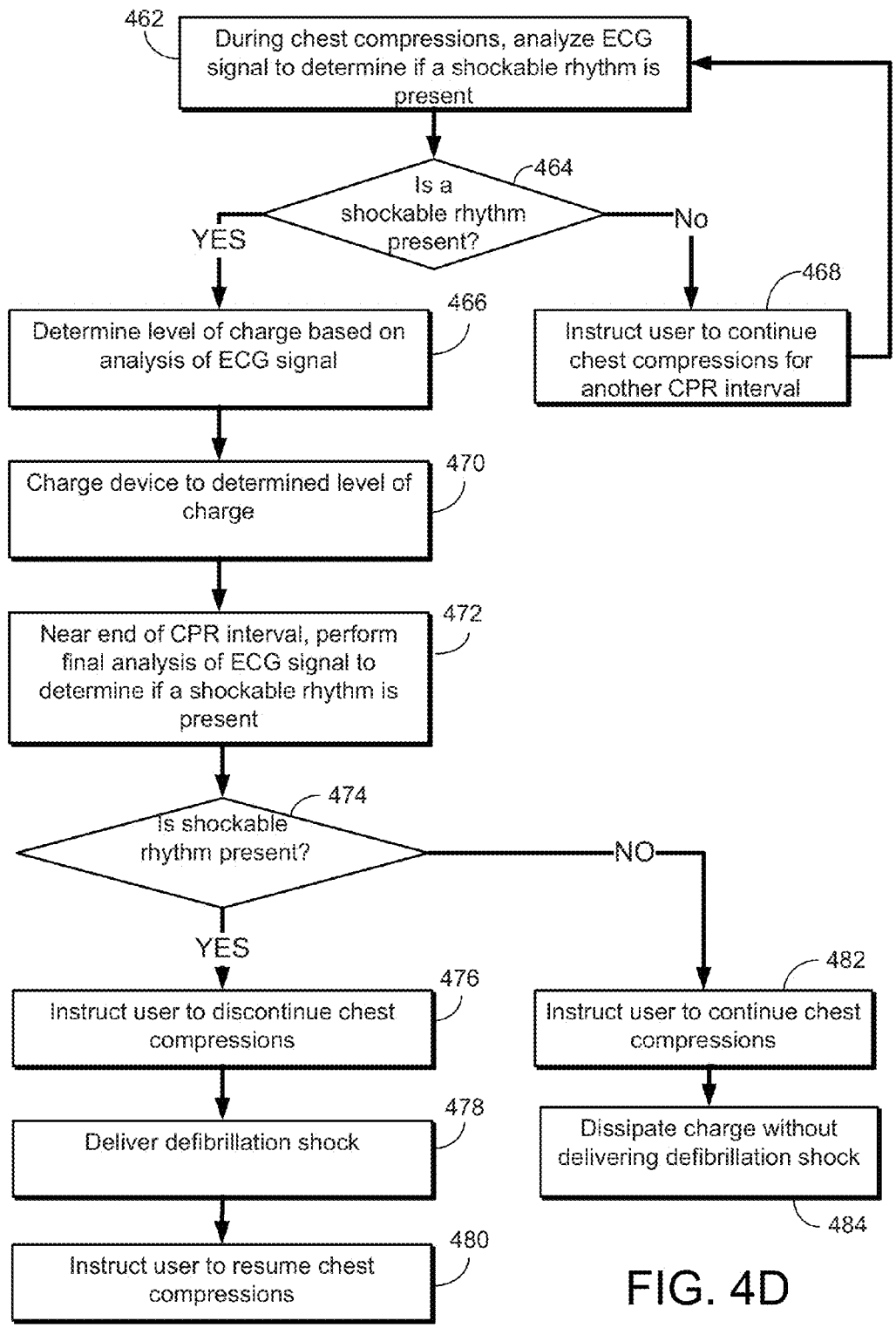
FIG. 4D is a flow chart showing actions taken to adaptively charge a defibrillation device to a level selected based on ECG analysis.

FIG. 4D is a flow chart showing actions taken to adaptively charge a defibrillation device to a level (e.g., a desired total voltage or charge) selected based on ECG analysis. For example, a level of charge for the defibrillation device (and a total amount of charge delivered to the victim) can be adaptively determined based on factors related to the ECG analysis such as the amplitude, frequency of the ECG signal, and/or an AMSA value. For example, if a victim is experiencing VF with a high amplitude ECG signal, only a low level of energy in the shock may be used. In contrast, in situations where it is not likely that conversion to a perfusing rhythm will occur with only a low energy shock such as situations in which the ECG signal exhibits a low amplitude, then the defibrillation device can be charged to a higher energy level. In some additional examples, a level of charge for the defibrillation device (and a total amount of charge delivered to the victim) can be adaptively determined based patient size (height, weight, BMI, and/or chest impedance) in addition to or as an alternative to determining the target charge based on the ECG analysis.

In some implementations, an amplitude magnitude spectrum area (AMSA) value can be used to determine how to charge the defibrillation device and when to administer a defibrillation shock. For example, a high AMSA value is believed to be correlated to a high likelihood of conversion to a perfusing rhythm. The AMSA value can be monitored and the level of shock and/or length of time chest compressions are administered can be modified based on a threshold AMSA value and/or trends observed in the AMSA value. For example, a shock could be administered when a change (e.g., a decrease) in the AMSA value is observed by systems provided in an AED device. The AMSA value can also be used to determine the rate in charging the defibrillator. For example, an AMSA number that is associated with an accuracy level of 70% or greater (e.g., 70%, 80%, 90%) in predicting a successful conversion can be associated with the fastest possible rate in charging the defibrillator; The lower value the AMSA number is, the rate of charging is set to (e.g., half speed in charging when an AMSA number associated with an accuracy level of 50% is observed).

In FIG. 4D at block 462, while chest compressions are being administered, the AED device analyzes an ECG signal, and at box 464, the AED device determines if a shockable rhythm is likely to be present in the victim at the end of the CPR interval. If a shockable rhythm is not likely to be present in the victim at the end of the CPR interval, the AED instructs the rescuer to continue chest compressions for another CPR interval at box 468 and continues to receive and analyze the ECG signals. If the system determines that a shockable rhythm is likely to exist, at box 466, the AED device determines a level of charge based on an analysis of the ECG signal. For example, the level of charge or the rate of charging can be based on an amplitude of the ECG signal, a frequency of the ECG signal, and/or and AMSA value of the ECG signal. The level of charge can vary from a low charge to a high charge. In general, if the AMSA value is used, the level of charge is inversely proportional to the AMSA value such that the device is charged to a lower level if the AMSA value is higher. At box 470, the AED charges the defibrillation device to the determined level of charge. The rate of charging can also vary from a slow charging rate to a fast charging rate: for example, if the AMSA value is used, the charging rate can be proportional to the AMSA value such that the device is charged faster if the AMSA value is higher.

At box 472, near the end of the CPR interval, the AED device performs a final analysis and determines (box 474) if a shockable rhythm is present. If a shockable rhythm does not exist, the AED instructs the rescuer to continue chest compressions at box 482 such that the victim receives uninterrupted chest compressions. At box 483, the AED dissipates the charge (e.g., using one or more of the methods described herein) from the defibrillation device without delivering a shock to the victim.

If a shockable rhythm is observed, at box 476, the AED instructs the rescuer to discontinue chest compressions (e.g., using one or more of the methods described herein). At box 478, the AED device delivers the shock and at box 480, the AED device instructs the user to resume chest compressions.

Other data besides ECG data may be included as part of the determination of whether a shockable rhythm exists and may be incorporated into the analysis algorithm, for instance pulse oximetry, capnography, respiration, impedance cardiography, and blood pressure measurements. At least some of the data may remain in the time domain without any Fourier or other transform method being performed on it. Pulse oximetry, impedance cardiography, and blood pressure measurements may be used to augment the ECG to determine if a pulse is present. Capnography may be used to determine the overall effectiveness of cardiopulmonary resuscitation. The additional measures can also include measurement of velocity or acceleration of chest compression during chest compressions according to the techniques taught by U.S. Pat. No. 7,220,335, Method and Apparatus for Enhancement of Chest Compressions During Chest Compressions, the contents of which are hereby incorporated by reference in their entirety and U.S. patent application Ser. No. 11/430,579 titled ECG rhythm advisory method the contents of which are hereby incorporated by reference in their entirety.

In some embodiments, the cross-correlation between the ECG signal (with CPR artifact) and the CPR signal (in the form of compression acceleration, velocity, or displacement) can be calculated. Based on the strength of the cross-correlation between the ECG signal and the CPR signal, the system can select an appropriate analysis method to remove the artifacts from the ECG signal and determining if a shockable rhythm exists in the ECG signal. For example, a high cross-correlation value between the ECG signal and the CPR signal indicates that the majority of the artifact is from the chest compression and thus an analysis method designed for ECG with CPR artifact may be more reliable than other analysis methods. Alternatively, a low cross-correlation value typically indicates that there is strong non-CPR-related artifact in the recorded ECG signal.

Figure 5A:
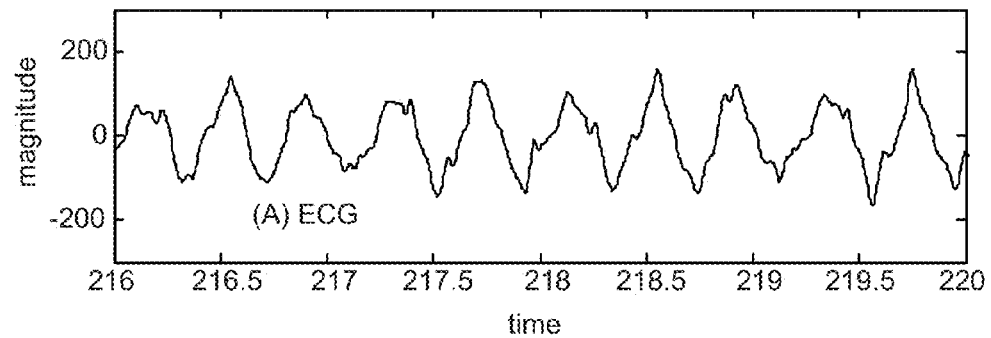
FIG. 5A is a diagram of and ECG signal.
Figure 5B:
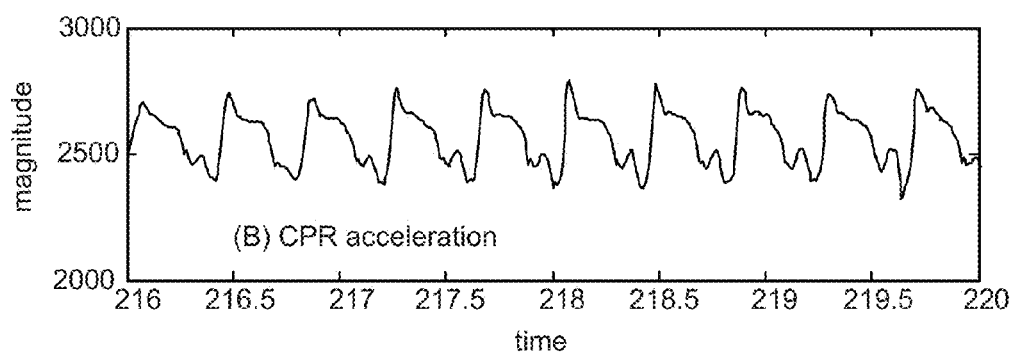
FIG. 5B is a diagram of a CPR acceleration signal showing strong cross-correlation with the ECG signal.

FIGS. 5A and 5B illustrate an example of the observed ECG signal (FIG. 5A) showing strong cross-correlation with the CPR acceleration signal (FIG. 5A), which indicates that the ECG signal is free from non-CPR noise. The strong cross correlation can be observed based on the similarity in the shape of the CPR signal and the ECG signal. The cross correlation can be computed automatically during the analysis of the ECG signal.

Figure 6A:
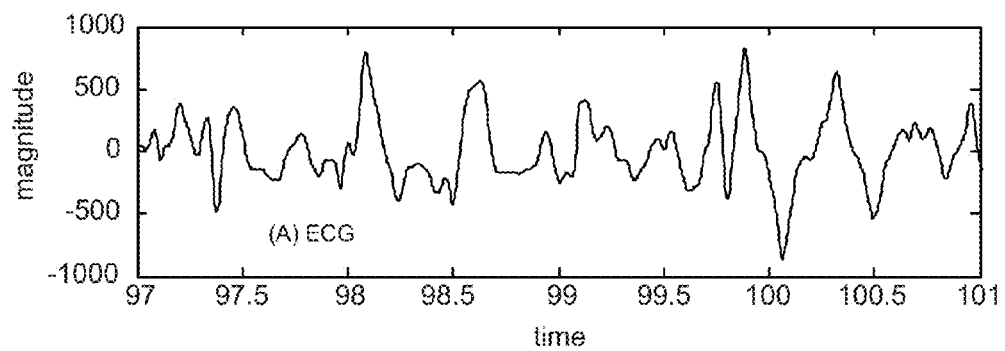
FIG. 6A is a diagram of and ECG signal.
Figure 6B:
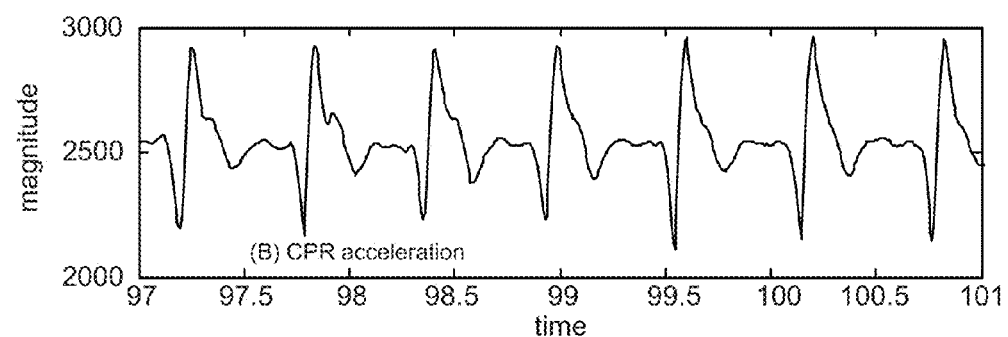
FIG. 6B is a diagram of a CPR acceleration signal showing low cross-correlation with the ECG signal.

As noted above, a low cross-correlation value between the ECG signal and the CPR signal typically indicates that there is strong non-CPR-related artifact in the recorded ECG signal. With the presence of the non-CPR-related artifact, the ECG analysis performed during CPR may be less reliable (or may not be reliable). Due to the lesser reliability of the ECG analysis, the system can utilize a longer period of CPR-free time in a re-confirmation analysis (e.g., a longer analysis period can be utilized after the cessation of CPR and prior to the determination of whether a shockable rhythm exists). FIGS. 6A and 6B illustrate an example of the observed ECG signal (FIG. 6A) with weak cross-correlation with the CPR acceleration signal (FIG. 6B). This indicates that the ECG has strong non-CPR noise and a longer of re-confirmation analysis period can be used.

The information processing technique can include but is not limited to simple combining rules or math, neural networks, expert systems incorporating fuzzy or standard logic, or other artificial intelligence techniques. For example, multiple factors can be combined to make a determination of whether to defibrillate. In some situations, even if a shockable rhythm exists (e.g., as determined based on the ECG analysis) the AED device may not recommend delivering the shock to the patient because one or more other factors suggest that another treatment would likely be more effective. For example, if a shockable rhythm exists but the quality of CPR chest compressions as measured based on one or more of the velocity, acceleration, or depth of the compressions is low, then the AED device could recommend continuing chest compressions to increase blood circulation rather than stopping the chest compressions to deliver the shock.

In some embodiments, the AED device can combine different measures and output results related to the desirability of defibrillation and/or the effectiveness of the chest compressions being delivered by the rescuer. Exemplary outputs can include statements such as "strong need for defibrillation," "weak need for defibrillation," "faster chest compressions needed," or "additional chest compressions needed."

In some embodiments, the AED device can deliver the defibrillation shock during the chest compression cycle (e.g., while the rescuer is delivering the chest compressions). For example, the AED can synchronize of the defibrillation shock to the chest compression cycle. Delivery of the defibrillation shock during the early portion (approximately the first 300 milliseconds) of the decompression (diastolic) phase of the chest compression cycle can improve the likelihood of success of the delivered shock. The decompression phase begins when the rescuer reduces compression force on the chest, allowing the chest to rise, and the heart to expand. The AED device can detect chest compression phase and timing information indicative of the start of the decompression phase and initiate delivery of the electromagnetic therapy within 300 milliseconds of the start of the decompression phase. In some embodiments, delivery of electromagnetic therapy can be initiated within 25-250 milliseconds of the start of the decompression phase. Circuitry and processing for the detection of chest compression phase timing information can include a pressure sensor and/or an accelerometer. Exemplary methods for synchronizing defibrillation with chest compression phase are described in U.S. patent application Ser. No. 12/263,813 titled Synchronization of Defibrillation and Chest Compressions, the contents of which are hereby incorporated by reference in their entirety.

Large self-adhesive electrode pads (~5" in diameter) are typically used to deliver defibrillation therapy to patients. The pads also provide ECG monitoring through the conductive surfaces that deliver therapy. In one implementation, additional small (~0.5" diameter) ECG electrodes can be integrated into the large pads.

In one embodiment, the two small ECG electrodes and large pads are configured such that there at least two mutually orthogonal ECG leads are generated. The vector sum of these leads generates a trajectory over time. The same methods for trajectory analysis described above may be used to analyze this trajectory as well.

Figure 7:
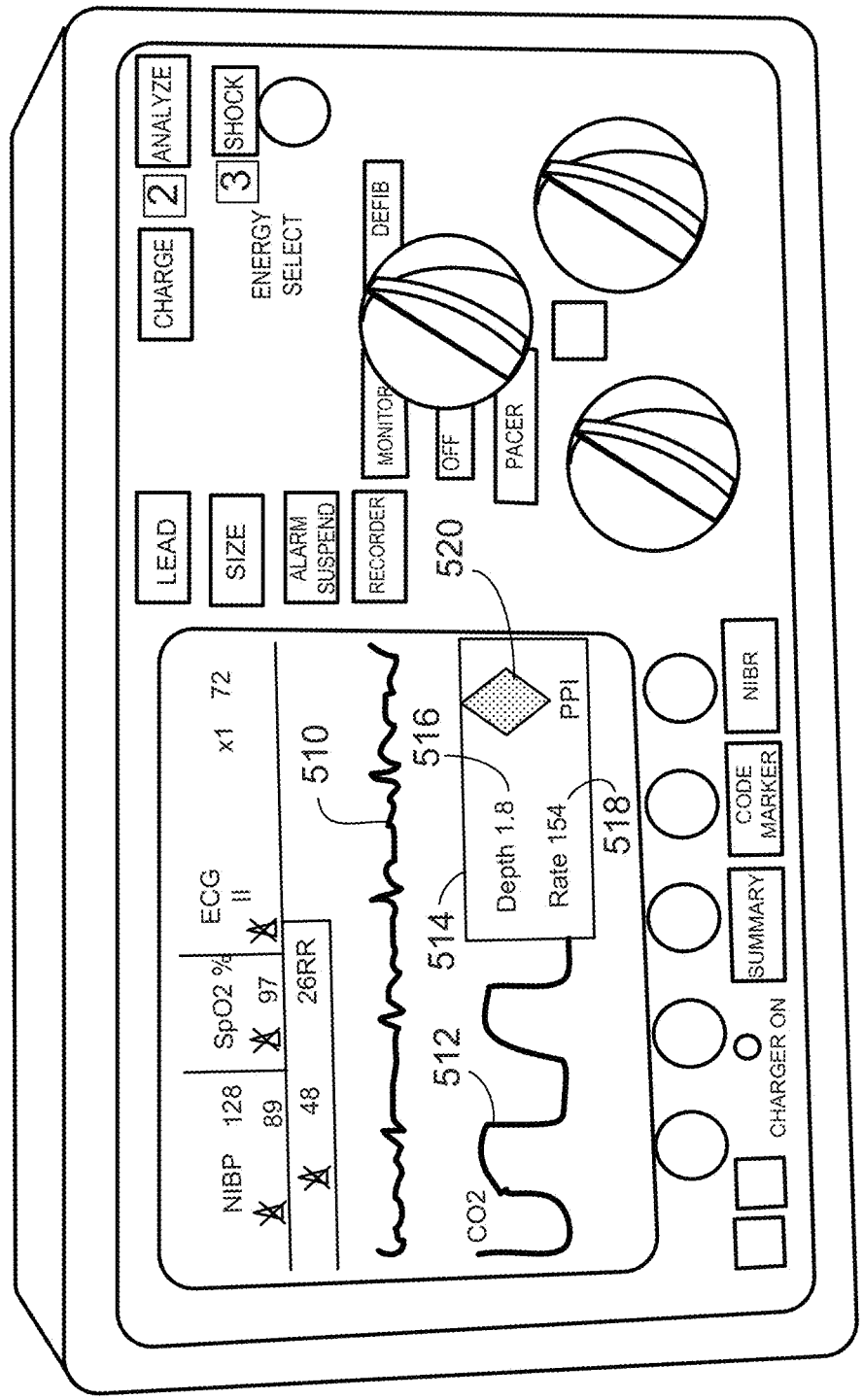
FIG. 7 is a diagram of a defibrillation device with a display.

FIG. 7 shows a defibrillation device 500 with a display portion 502 that provides information about patient status and CPR administration quality during the use of the defibrillator device. The data is collected and displayed in an efficient and effective manner to a rescuer. As shown on display 502, during the administration of chest compressions, the device 500 displays information about the chest compressions in box 514 on the same display as a filtered ECG waveform 510 and a CO2 waveform 512 (alternatively a SpO2 waveform can be displayed).

During chest compressions, the ECG waveform is generated by gathering ECG data point and accelerometer readings and filtering the motion induced (e.g., CPR induced) noise from the ECG waveform. Measurement of velocity or acceleration of chest compression during chest compressions can be performed according to the techniques taught by U.S. Pat. No. 7,220,335, Method and Apparatus for Enhancement of Chest Compressions. During Chest Compressions, the contents of which are hereby incorporated by reference in their entirety. Displaying the filtered ECG waveform helps clinicians reduce interruptions in CPR because the displayed waveform is easier for the rescuer to decipher. If the ECG waveform is not filtered, artifacts from manual chest compressions make it difficult to discern the presence of an organized heart rhythm unless compressions are halted. Filtering out this artifact allows clinicians to view the underlying rhythm without stopping chest compressions.

The CPR information in box 514 is automatically displayed when compressions are detected. The information about the chest compressions displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to or instead of an indication of whether the values are within or outside of an acceptable range) is believed to provide useful feedback to the rescuer. For example, if an acceptable range for chest compression depth is between 1.5-2 inches, providing the rescuer with an indication that his/her compressions are only 0.5 inches can allow the rescuer to determine how to correctly modify his/her administration of the chest compressions.

The information about the chest compressions displayed in box 514 also includes a perfusion performance indicator (PPI) 520. The PPI 520 is a shape (e.g., a diamond) with the amount of fill in the shape differing to provide feedback about both the rate and depth of the compressions. When CPR is being performed adequately, for example, at a rate of about 100 compressions/minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

As shown in display 500, the filtered ECG waveform 510 is a full length waveform filling the entire span of the display device while the second waveform (e.g., the CO2 waveform 512) is a partial length waveform and fills only a portion of the display. A portion of the display beside the second waveform provides the CPR information in box 514. For example, the display splits the horizontal area for the second waveform in half, displaying waveform 512 on left and CPR information on the right in box 514.

The data displayed to the rescuer can change based on the actions of the rescuer. For example, the data displayed can differ based on whether the rescuer is currently administering CPR chest compressions to the patient. Additionally, the ECG data displayed to the user can change based on the detection of CPR chest compressions. For example, the adaptive filter can automatically turn ON or OFF based on detection of whether CPR is currently being performed. When the filter is on (during chest compressions), the filtered ECG data is displayed and when the filter is off (during periods when chest compressions are not being administered) unfiltered ECG data is displayed. An indication of whether the filtered or unfiltered ECG data is displayed can be included with the waveform.

Figure 8A:
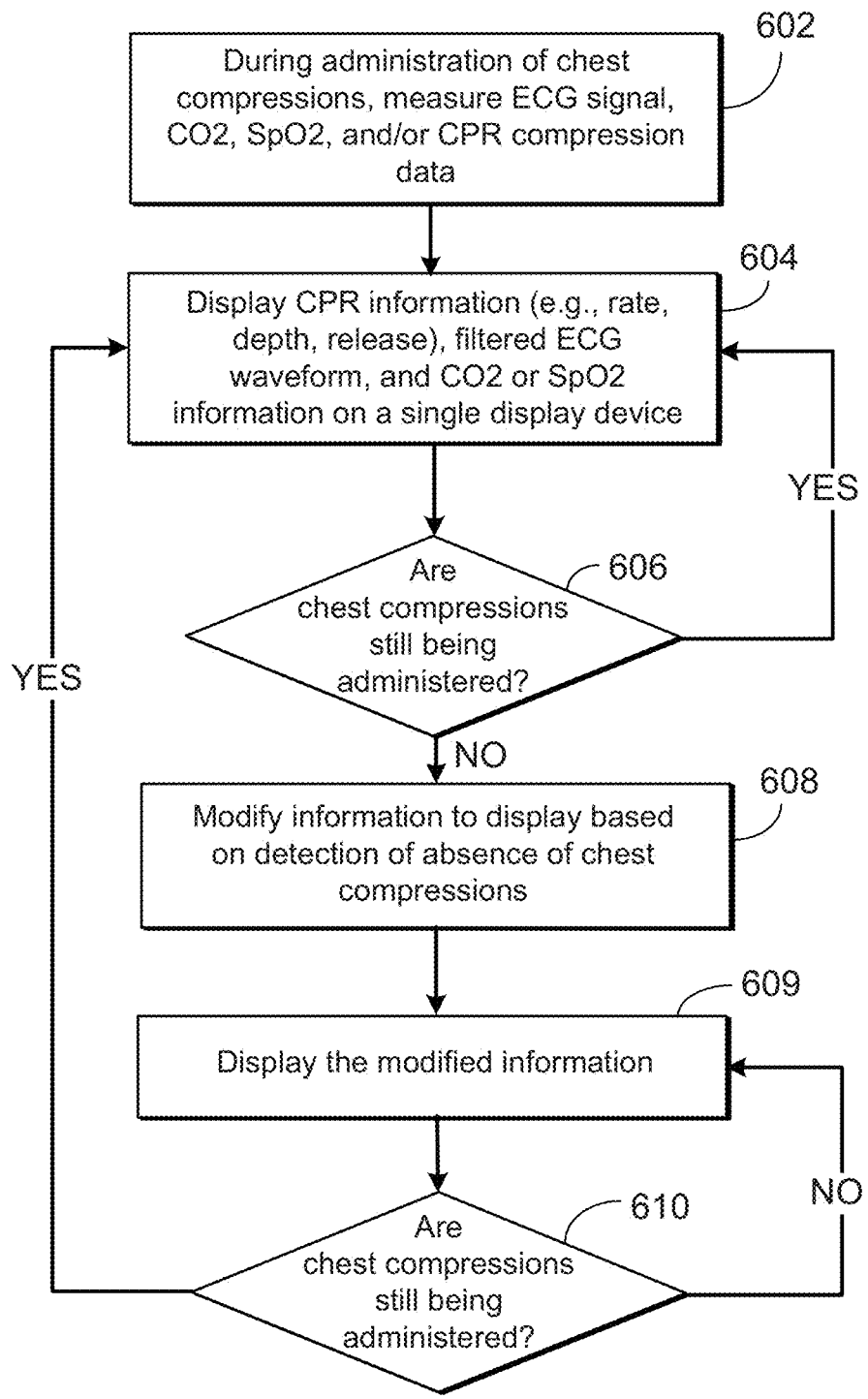
FIG. 8A is a flow chart showing actions taken to modify information presented on a display of a defibrillation device based on the detection of CPR chest compressions.

FIG. 8A is a flow chart showing actions taken to modify information presented on a display of a defibrillation device based on the detection of CPR chest compressions. The exemplary process begins at box 602 with collection of various data during the administration of chest compressions. The measurements can include measurement of EGC signals, CO2, SpO2, and/or CPR chest compression quality measurements such as depth, rate, and release information. At box 604, the defibrillator device displays CPR information, a filtered ECG waveform, and a second waveform such as CO2, SpO2, or chest compressions on the display device. As described above, displaying this combination of information on a single display device during CPR administration provides an easy to view summary of the patient status and CPR quality.

At box 606, the defibrillation device determines whether CPR chest compressions are still being administered. For example, data collected from an accelerometer can be used to determine whether the rescuer is still administering chest compressions. If the user is still administering chest compressions, the system continues to display the CPR information, the filtered ECG waveform, and the second waveform. If the defibrillation device detects that the rescuer has ceased administration of chest compressions, at box 608, the defibrillation device modifies the information to present on the display and at box 609 displays the modified information. An exemplary modification of the information presented on the display can include automatically switching from a filtered ECG waveform to an unfiltered ECG waveform upon the detection of the cessation of chest compressions.

At box 610, the defibrillation device determines whether chest compressions have been resumed. If chest compressions have not been resumed, the defibrillation device continues to display the information from the modified display 609. If chest compressions have been resumed, the defibrillation device modifies the display to revert back to showing the CPR information, filtered ECG waveform, and the CO2 or SpO2 waveform.

Figure 8B:
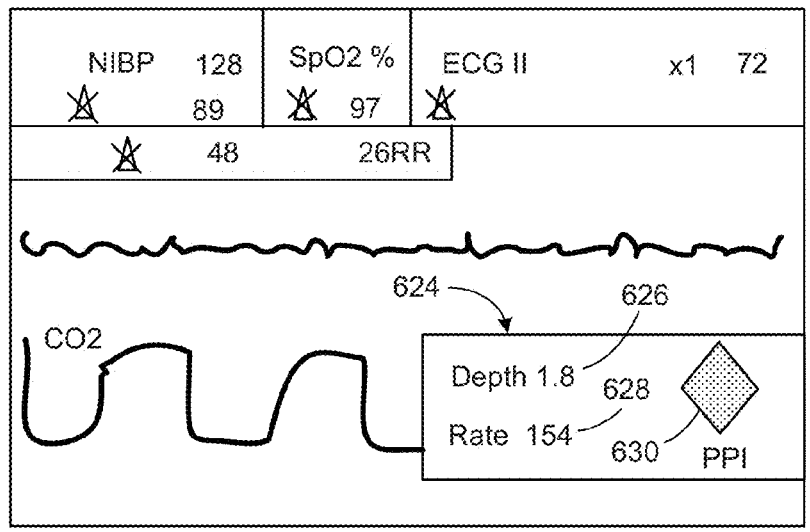
FIGS. 8B-8E show screenshots showing exemplary information presented on a defibrillator display.
Figure 8C:
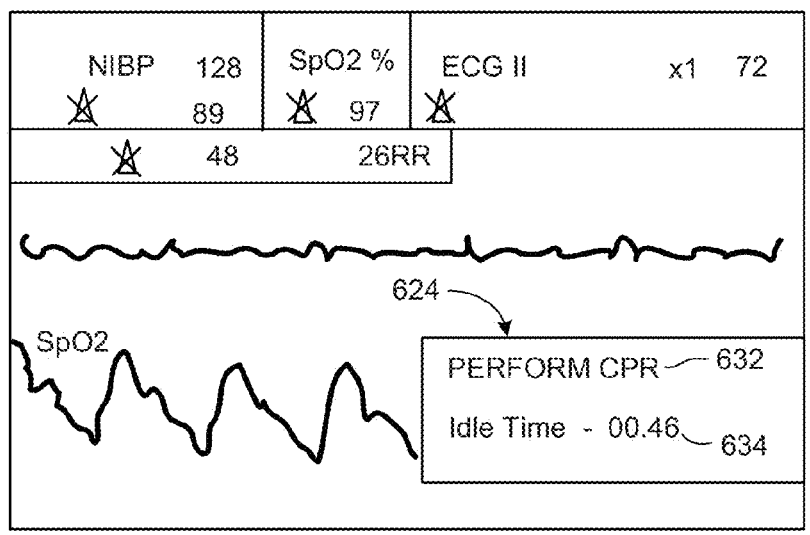
Figure 8D:
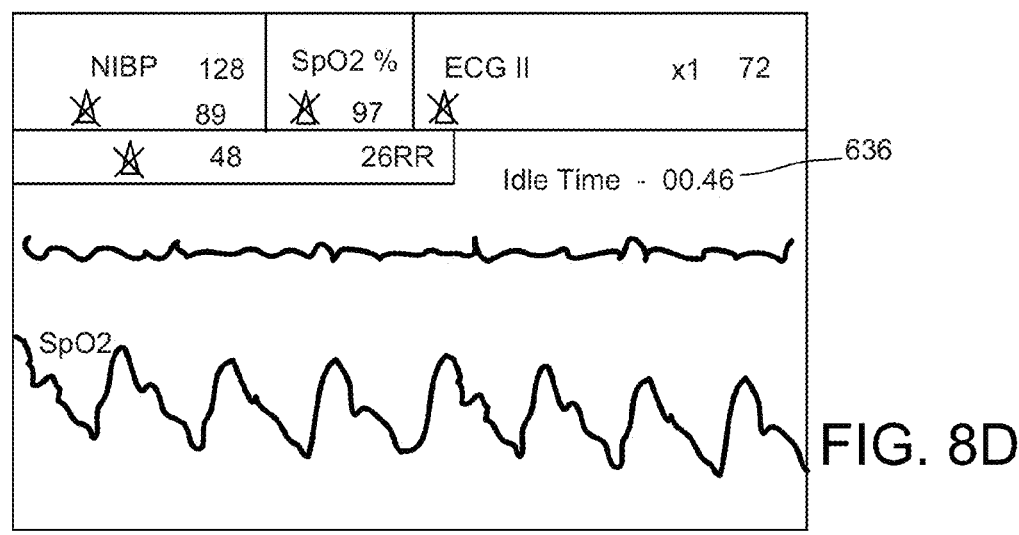

FIG. 8B shows exemplary information displayed during the administration of CPR chest compressions while FIGS. 8C and 8D show exemplary information displayed in the absence of CPR chest compressions. The defibrillation device automatically switches the information presented based on whether chest compressions are detected.

An exemplary modification of the information presented on the display can include automatically switching one or more waveforms displayed. In one example, the type of measurement displayed can be modified based on the presence or absence of chest compressions. For example, CO2 or depth of chest compressions may be displayed (e.g., a CO2 waveform 620 is displayed in FIG. 8B) during CPR administration and upon detection of the cessation of chest compressions the waveform can be switched to display a SpO2 or pulse waveform (e.g., an SpO2 waveform 622 is displayed in FIG. 8C).

Another exemplary modification of the information presented on the display can include automatically adding/removing the CPR information from the display upon detection of the presence or absence of chest compressions. As shown in FIG. 8B, when chest compressions are detected, a portion 624 of the display includes information about the CPR such as depth 626, rate 628 and PPI 630. As shown in FIG. 8C, when CPR is halted and the system detects the absence of CPR chest compressions, the defibrillation device changes the CPR information in the portion 624 of the display to include an indication 632 that the rescuer should resume CPR and an indication 634 of the idle time since chest compressions were last detected. In other examples, as shown in FIG. 8D, when CPR is halted, the defibrillation device can remove the portion of the display 624 previously showing CPR data and can display a full view of the second waveform. Additionally, information about the idle time 636 can be presented on another portion of the display.

Figure 8E:
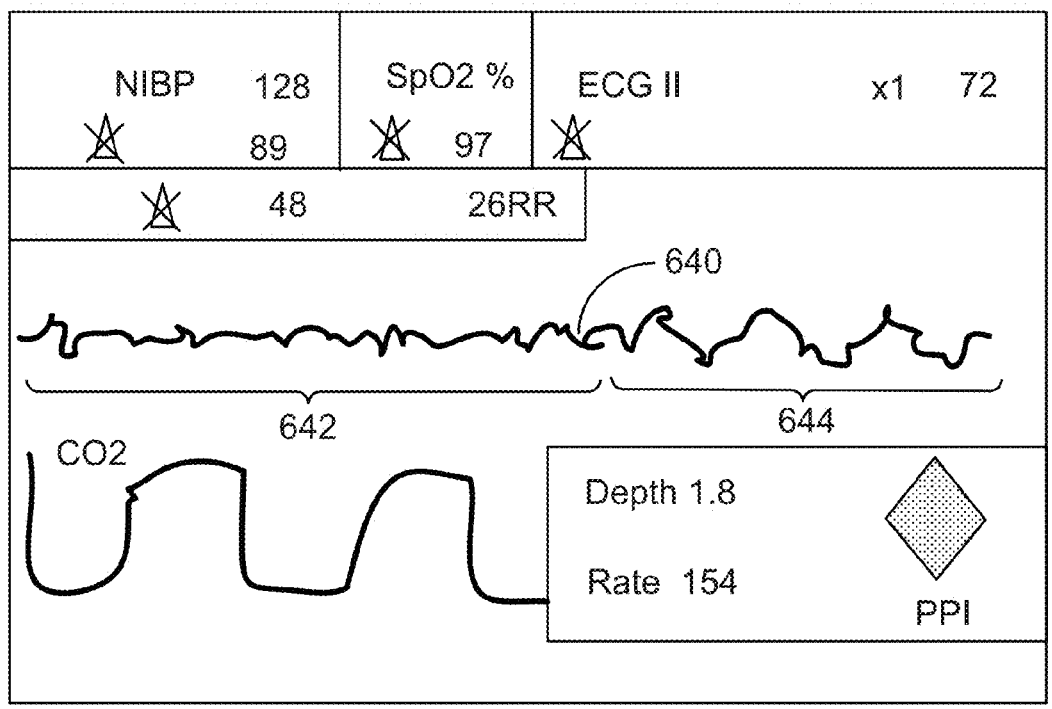
Figure 9A:
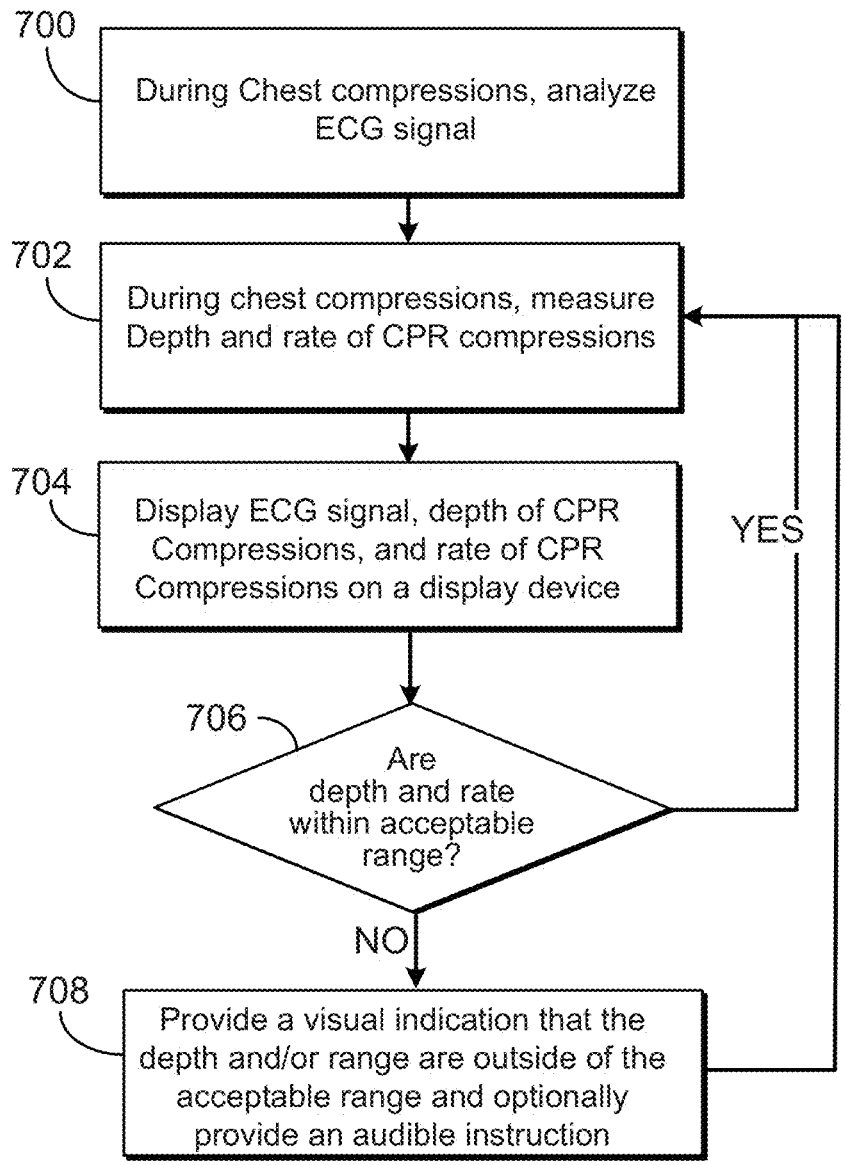
FIG. 9A is a flow chart showing actions taken to provide an indication of CPR quality on a display of a defibrillator device.

In some examples, the defibrillator device automatically switches between a filtered and an unfiltered ECG waveform based on the presence or absence of chest compressions. For example, an ECG waveform without filtering can be displayed when chest compressions are not detected while a filtered ECG waveform can be displayed when chest compressions are detected. For example, FIG. 8E shows an ECG waveform 640 at the time chest compressions are first initiated. A first portion 644 of the ECG waveform displays an unfiltered ECG signal. When the defibrillator device determines that chest compressions are being performed, the device filters the ECG signal and displays a filtered ECG signal as shown in portion 642. FIG. 9A is a flow chart showing actions taken to provide an indication of CPR quality on a display of a defibrillator device. At box 700, during CPR chest compressions the defibrillator device analyzes an ECG signal and at box 702 the defibrillator device collects information about chest compressions by measuring depth and rate of compressions. The depth and rate of compressions can be determined based on measurements collected by an accelerometer. At box 704, the defibrillator device displays a filtered ECG signal, information about the depth of CPR chest compressions, and information about the rate of CPR chest compressions on a single user interface. At box 706, the defibrillator device determines whether the depth and rate of CPR chest compressions are within acceptable ranges by comparing the depth and rate measurements to threshold values that indicate acceptable values for the depth and rate. If the defibrillator device determines that the depth and rate are within an acceptable range, the defibrillator device continues to monitor the quality of chest compressions. On the other hand, if the defibrillator device determines that the depth and rate are outside of the acceptable range, the defibrillator device modifies the display to provide a visual indication that the depth and rate are outside of the acceptable range. The visual indication can be provided in various ways such as a graphical representation, a highlighting of particular values that are outside of the acceptable ranges, and/or a change in the color in which certain information is displayed. For example, if the depth or rate is within the acceptable range the value could be displayed in green font, if the depth or rate is near the boundaries of the acceptable range the value could be displayed in yellow font, and if the depth or rate is outside of the acceptable range the value could be displayed in red font. Other colors or indicators can be used.

Figure 9B:
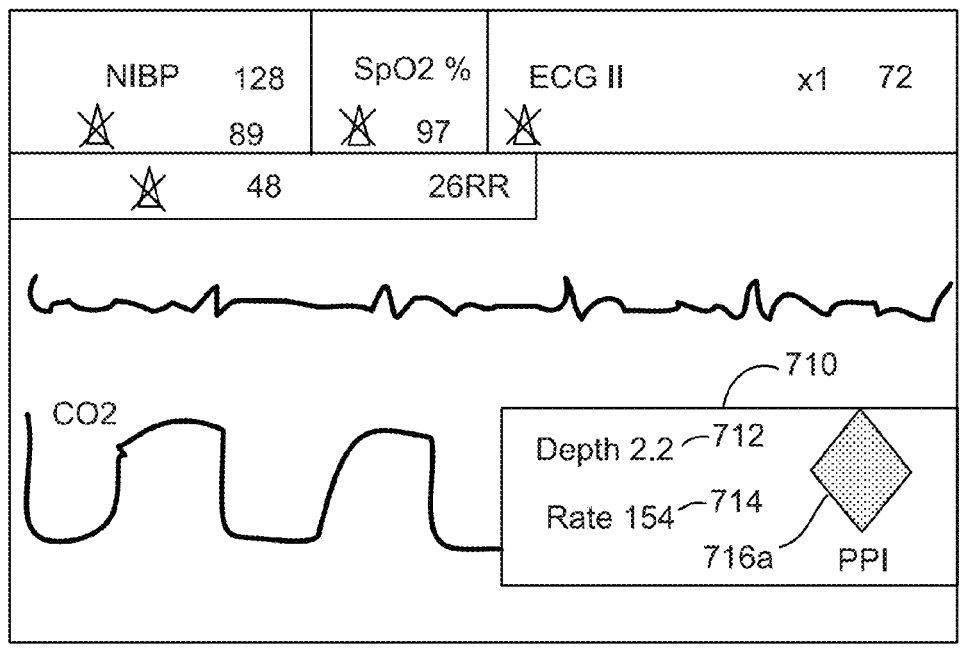
FIGS. 9B and 9C are screenshots showing exemplary information presented on a defibrillator display.
Figure 9C:
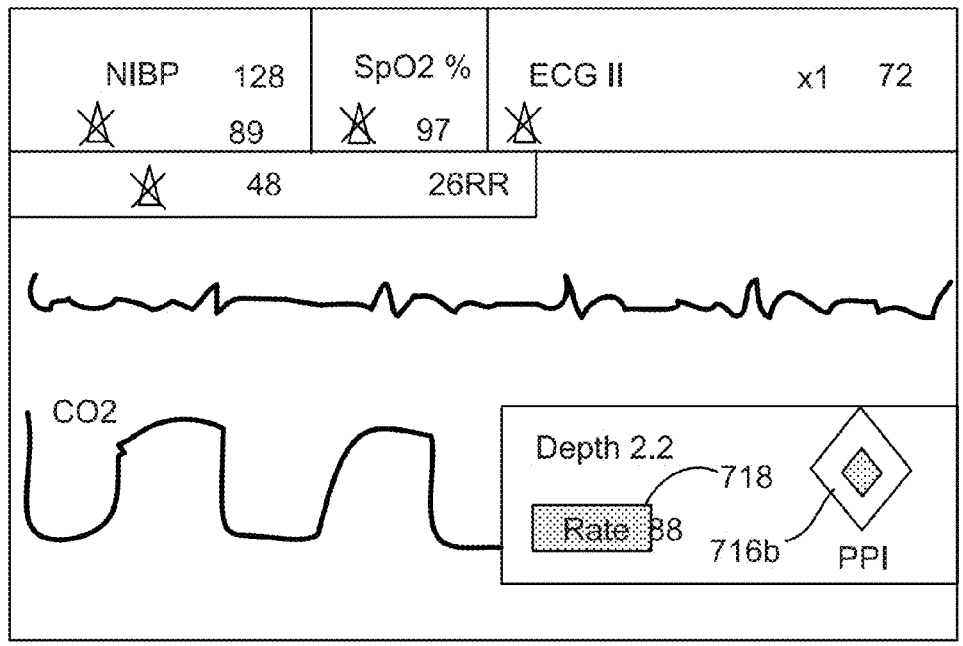

FIG. 9B shows exemplary data displayed during the administration of CPR chest compressions when the CPR quality is within acceptable ranges while FIG. 9C shows modifications to the display when the CPR quality is outside of the acceptable range.

In the example shown in FIG. 9C, the rate of chest compressions has dropped from 154 compressions per minute (FIG. 9B) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 718 to emphasize the rate information. In this example, the visual indication 718 is a highlighting of the rate information. Similar visual indications can be provided based on depth measurements when the depth of the compressions is more shallow or deeper than an acceptable range of depths.

In the examples shown in FIGS. 9B and 9C, a perfusion performance indicator (PPI) 716 provides additional information about the quality of chest compressions during CPR. The PPI 716 includes a shape (e.g., a diamond) with the amount of fill in the shape differing based on the measured rate and depth of the compressions. In FIG. 9B, the depth and rate fall within the acceptable ranges (e.g., at least 100 compressions/minute (CPM) and the depth of each compression is greater than 1.5 inches) so the PPI indicator 716a shows a fully filled shape. In contrast, in FIG. 9C when the rate has fallen below the acceptable range, the amount of fill in the indicator 716b is lessened such that only a portion of the indicator is filled. The partially filled PPI 716b provides a visual indication of the quality of the CPR is below an acceptable range.

In addition to measuring information about the rate and depth of CPR chest compressions, in some examples the defibrillator device provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial.

Figure 10A:
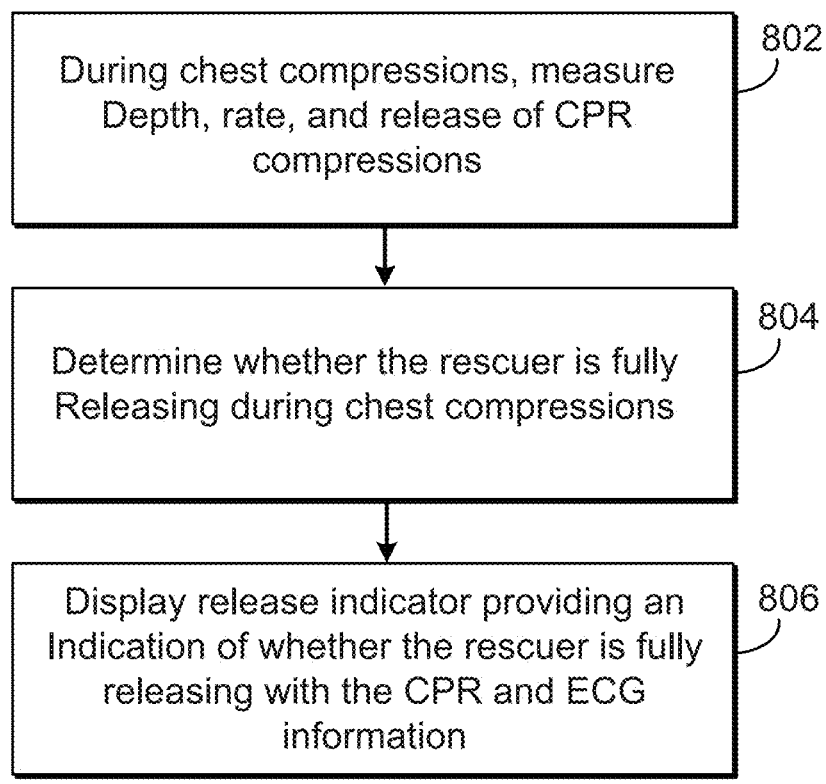
FIG. 10A is a flow chart showing actions taken to provide a release indicator.
Figure 10B:
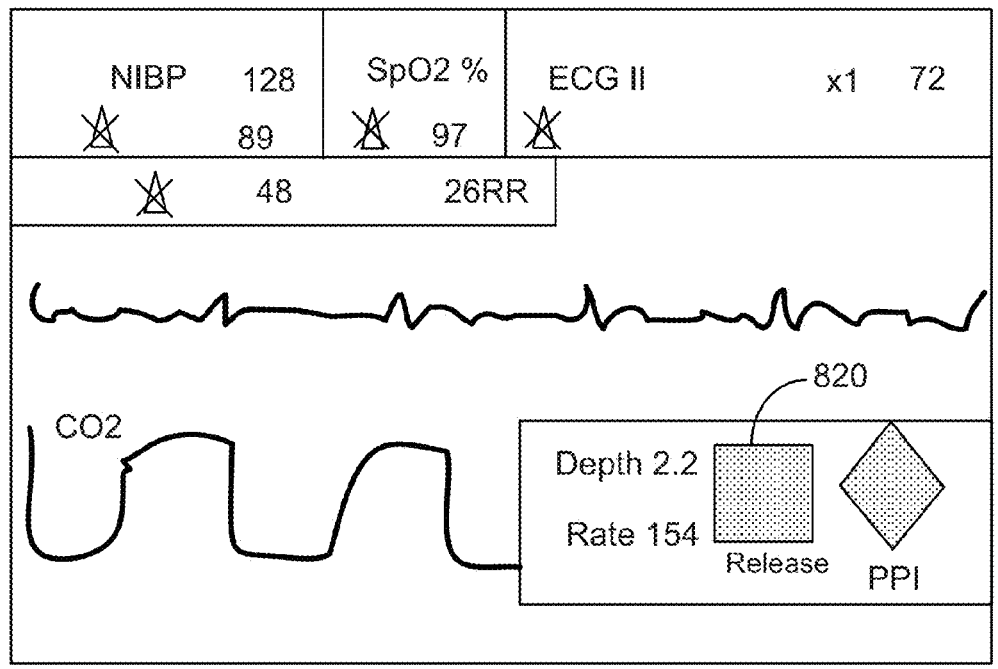
FIGS. 10B and 10C are screenshots showing exemplary information presented on a defibrillator display.
Figure 10C:
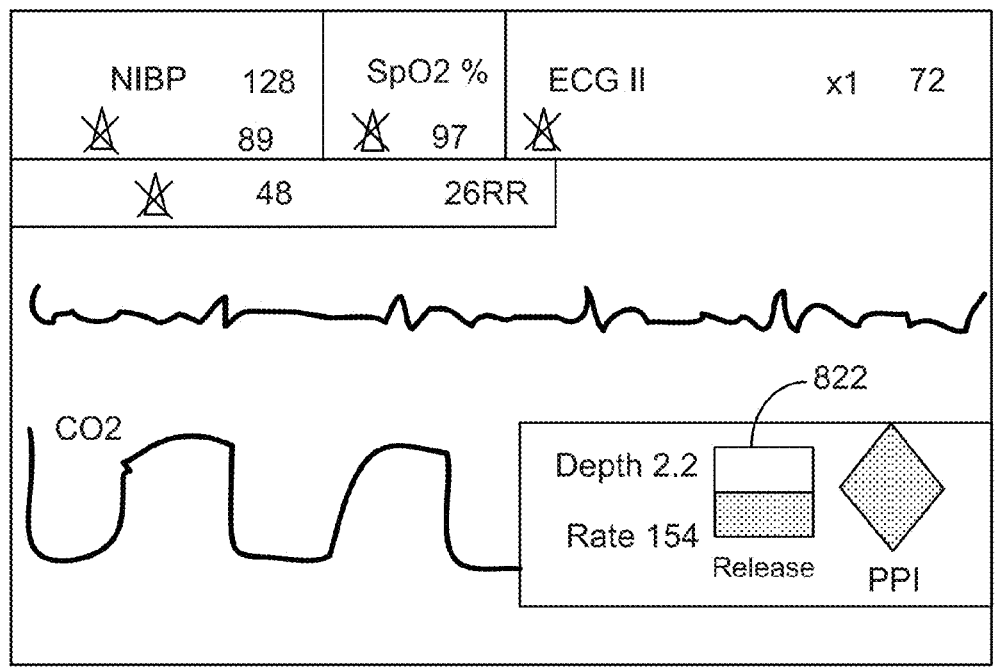

FIG. 10A is a flow chart showing actions taken to provide an indication of whether a rescuer is fully releasing between chest compressions. At box 802, the defibrillator device measures depth, rate, and release of CPR chest compressions. The depth, rate, and release of CPR chest compressions can be determined based on information collected from an accelerometer. Based on the collected information, at box 804, the defibrillator determines whether the rescuer is fully releasing between chest compressions. At box 806, the defibrillator provides an indicator on a display that includes information about whether the rescuer is fully releasing. For example, the display on the defibrillator can include a release indication box where the amount of fill in the box varies to indicate whether the rescuer is fully releasing between chest compressions. For example, as shown in FIG. 10B, when the rescuer is fully releasing the box 820 can be fully filled. When the rescuer is not fully releasing the amount of fill in the release indication box is decreased such that the box is only partially filled (e.g., as shown in box 822 of FIG. 10C).

Figure 11:
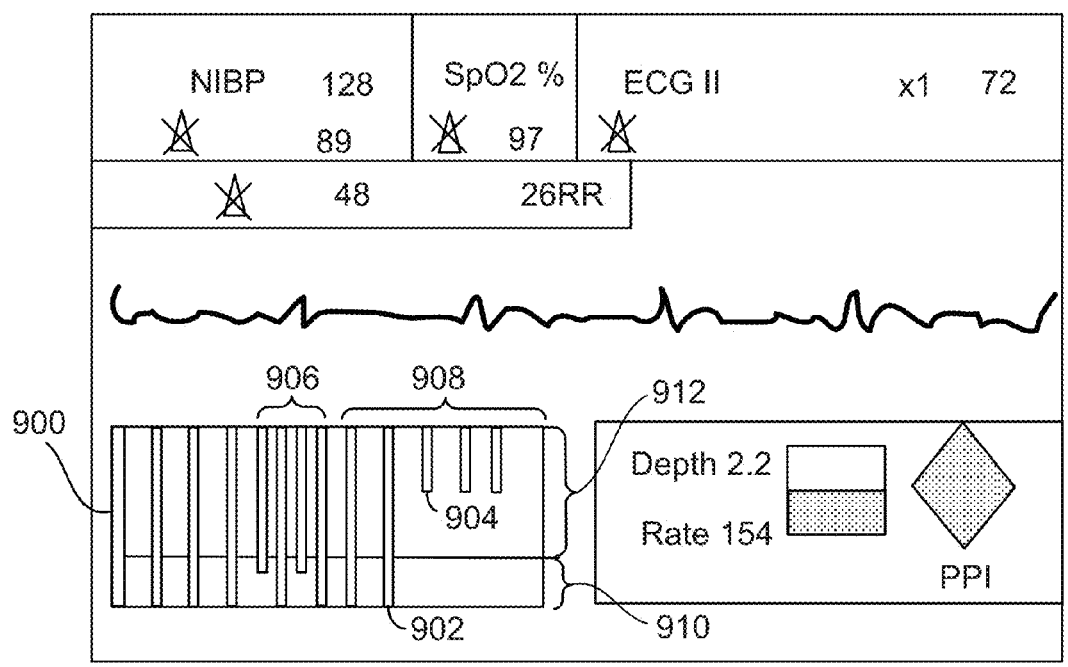
FIG. 11 is a screenshot showing exemplary information presented on a defibrillator display.

As shown in FIG. 11, in some examples, a visual representation of CPR quality in a CPR Compression bar graph 900. The CPR Compression Bar Graph 900 can be automatically displayed upon detection of CPR chest compressions.

In the CPR compression bar graph 900, the extent or height of a particular bar conveys information about a depth of compression. For example, bar 902 has a greater extent than bar 904 indicating that the depth of the compression associated with bar 902 was greater than the depth of the compression associated with bar 904. Ranges of preferred depths can be indicated by horizontally extending lines on the CPR compression bar graph 900. The lines can provide an indication of acceptable depths (e.g., region 910) and depths that are too shallow (e.g., region 912). Additionally, compressions falling outside of the acceptable range can be highlighted in a different color than compressions falling within the acceptable range of compression depth.

In the CPR compression bar graph 900, the y-axis represents time and each compression is displayed to allow the rescuer to view the rate of compressions. For example, region 906 includes closely spaced bars in comparison to region 908 indicating that the rate of chest compressions was greater in the time period associated with region 906 than in the time period associated with region 908.

Figure 12A:
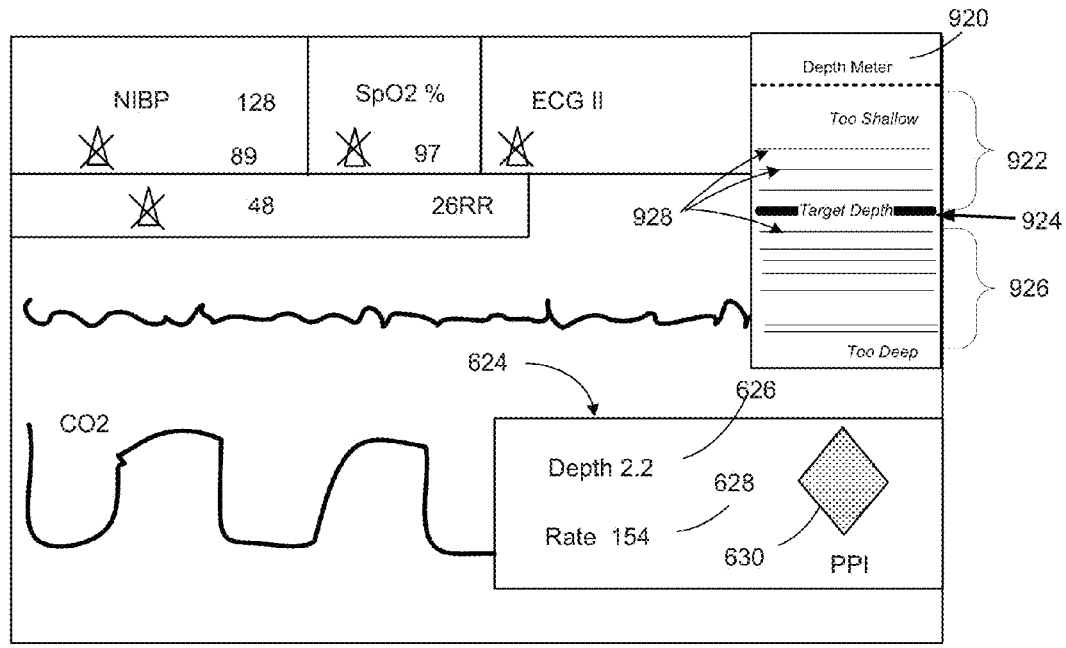
FIG. 12A is a screenshot showing exemplary information presented on a defibrillator display.

In some additional examples, as shown in FIG. 12A, a visual representation of CPR quality can include an indicator of CPR compression depth such as a CPR depth meter 920. The CPR depth meter 920 can be automatically displayed upon detection of CPR chest compressions.

On the CPR depth meter 920, depth bars 928 visually indicate the depth of the administered CPR compressions relative to a target depth 924. As such, the relative location of the depth bars 928 in relation to the target depth 924 can serve as a guide to a rescuer for controlling the depth of CPR compressions. For example, depth bars 928 located in a region 922 above the target depth bar 924 indicate that the compressions were more shallow than the target depth and depth bars 928 located in a region 926 below the target depth bar 924 indicate that the compressions were deeper than the target depth.

Figure 12B:
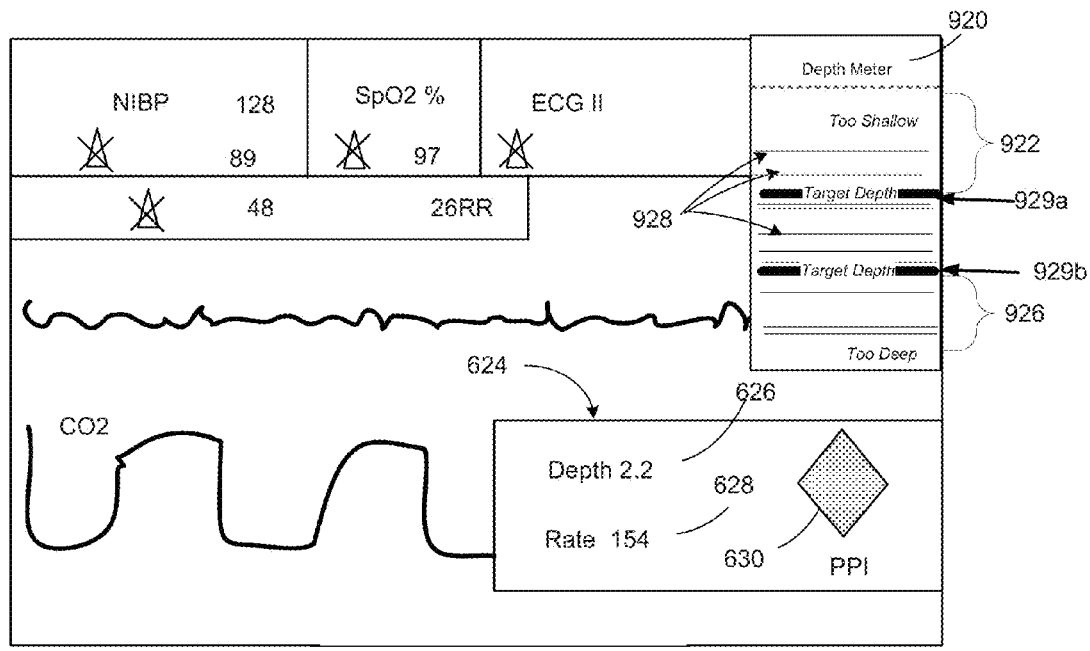
FIG. 12B is a screenshot showing exemplary information presented on a defibrillator display.

While the example shown in FIG. 12A displayed the target depth 924 as a single bar, in some additional examples, the target depth can be displayed as a range of preferred depths. For example, two bars 929a and 929b can be included on the depth meter 920 providing an acceptable range of compression depths (e.g., as shown in FIG. 12B).

Additionally, in some examples, compressions having depths outside of an acceptable range can be highlighted in a different color than compressions having depths within the acceptable range of compression depths.

The depth bars 928 displayed on the CPR depth meter 920 can represent the compression depths of the most recent CPR compressions administered by the rescuer. For example, the CPR depth meter 920 can display depth bars 928 for the most recent 10-20 CPR compressions (e.g., the most recent 10 CPR compressions, the most recent 15 compressions, the most recent 20 CPR compressions). In another example, CPR depth meter 920 can display depth bars 928 for CPR compressions administered during a particular time interval (e.g., the previous 10 seconds, the previous 20 seconds).

In some additional embodiments, physiological information (e.g., physiological information such as end-tidal $CO_2$ information, arterial pressure information, volumetric CO2, pulse oximetry (presence of amplitude of waveform possibly), carotid blood flow (measured by Doppler) can be used to provide feedback on the effectiveness of the CPR delivered at a particular target depth. Based on the physiological information the system can automatically adjust a target CPR compression depth (e.g., calculate or look-up a new CPR compression target depth) and provide feedback to a rescuer to increase or decrease the depth of the CPR compressions. Thus, the system can provide both feedback related to how consistently a rescuer is administering CPR compressions at a target depth and feedback related to whether the target depth should be adjusted based on measured physiological parameters.

In some examples, the system regularly monitors and adjusts the target CPR compression depth. In order to determine a desirable target depth, the system makes minor adjustments to the target CPR compression depth and observes how the change in compression depth affects the physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by between 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time the system can observe the physiological parameters and based on trends in the physiological parameters without making further adjustments to the target compression depth and at the end of the set time period determine whether to make further adjustments to the target compression depth.

Figure 13:
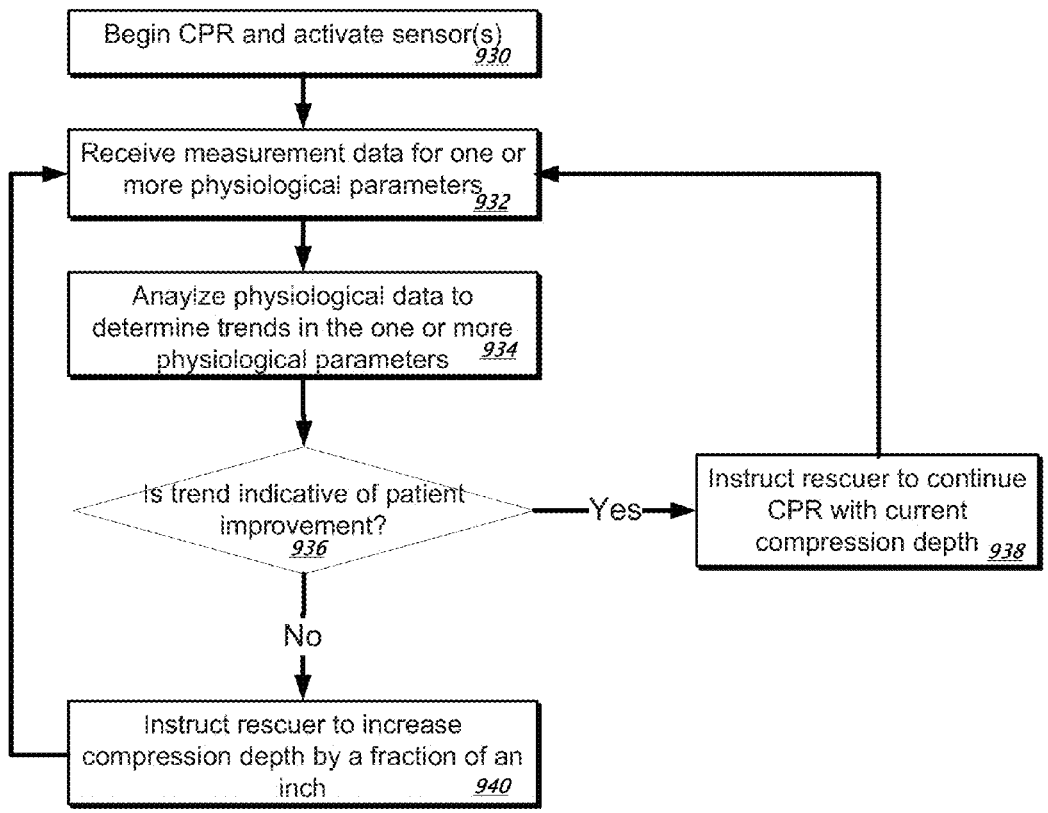
FIG. 13 is a flow chart showing actions taken to adjust a target compression depth by a fraction of an inch.

FIG. 13 is a flowchart of a process for providing feedback to a rescuer who is administering manual CPR chest compressions to a victim. In general, the process involves deploying various medical devices at the scene of an emergency and providing feedback to the rescuer in relation to administration of CPR to the victim.

The process begins at box 930, where the rescuer begins administration of manual CPR and various sensors are activated. A communication link is also established between the sensor and a feedback unit, which may be in the form of a tablet, like tablet 116 in FIG. 2, or a defibrillator like defibrillator 112 in FIG. 2. The communication may occur automatically upon activating the two communicating components, such as by instigating an automatic BLUETOOTH or WiFi connection in a familiar manner.

At box 932, measurement data for one or more physiological parameters for the victim is collected by one or more sensor devices. Measured physiological parameters can include, for example, end-tidal $CO_2$ information from a capnometer, arterial pressure information from an arterial line in a radial artery of the victim. Such information about the physiological parameters may be passed from the sensors to a computing component, such as a compression depth determination unit.

At box 934, the system analyzes the received physiological information and determines trends in the physiological information (e.g., determines whether the physiological information indicates that the victim is improving, deteriorating, or remains stable). In some examples, the analysis can include calculating the derivative of the physiological information to determine whether there is a positive or negative slope. At box 936, the determined trend data is used to determine whether a trend shows patient improvement. For example, patient status can be determined based on whether the slope is positive or negative. Upon the device making such determinations, the device provides feedback to the rescuer in applying CPR compressions. For example, the feedback can be visual or audible feedback to guide a rescuer regarding whether to administer CPR compressions at the same depth or to adjust the depth of the administered CPR compressions.

More particularly, as shown in box 938, if the system determines that the trend in the physiological information is indicative of patient improvement, the system provides a visual or audio indicator to instruct the rescuer to continue to administer CPR compressions at the current target depth and returns to receiving physiological data and analyzing newly gathered physiological data (box 932, 934). On the other hand, if the system determines that the trend in the physiological information is not indicative of patient improvement, the system instructs the rescuer to increase the CPR compression depth by a fraction of an inch (e.g., 0.15-0.25 inches) and returns to receiving physiological data and analyzing the newly gathered physiological data (box 932, 934). In some additional examples (not shown), the system could also determine that the trend in physiological information is indicative of the return of spontaneous circulation (ROSC) and recommend the cessation of compressions. For example, such a determination could be made during pauses in compressions—if BP, arterial pressure, CO2, spo2, etc are maintained with compression pauses, the patient likely has ROSC.

In some embodiments, the system can iteratively determine whether to adjust the target compression depth at predetermined time intervals. Because many physiological parameters respond slowly to changes in CPR compression depth, the length of the time interval can be selected to allow observation of a change in the physiological parameter based on a current compression depth prior to determining whether to modify the target compression depth.

In some examples, the system executes dual feedback loops. The first feedback loop is executed at a first rate and provides periodic feedback to a rescuer about chest compressions performed by the rescuer (e.g., about the depth of the chest compressions compared to the current target depth). The second feedback loop is executed at a second rate that is slower than the first rate and is used to determine whether to adjust content of the periodic feedback (e.g., whether to adjust the target compression depth). As such, in one example, the dual feedback loops provide multiple instances of feedback to the rescuer regarding the depth of the chest compressions performed by the rescuer for each instance of determining whether to adjust the target compression depth.

For example, during an initial time period of compressions (e.g., the first minute) the system compares observed CPR compression depths to a target compression depth of 2 inches, or other depth determined by an established guideline that is either the result of a standards or guidelines group like the American Heart Association, or is the result of a particular physician's guidance in the local medical system. During this time, the system determines whether the rescuer is administering compressions within an acceptable depth range from the target compression depth of 2 inches (e.g., 90% of compressions are within 10% of the target depth) and provides feedback to assist the rescuer to administer CPR compressions at the target depth. During this time, the system also receives information about one or more physiological parameters and determines if the target CPR compression depth is effective (e.g., performs calculations to determine whether certain thresholds are satisfied and/or whether the observed values for the physiological parameters are improving). At the end of the initial time period, the system updates the target CPR compression depth based on the information about the physiological parameter, stored the updated target depth, and provides information about the updated target CPR compression depth to the rescuer. After the initial time period, the system continues to provide feedback to the rescuer both on whether the rescuer is properly administering compressions at the target depth and about whether the target depth should be modified. The information about whether the target depth should be modified may be determined and provided to the rescuer less frequently than the information about whether the rescuer is properly administering compressions at the target depth. The less frequent determination of modifications to the target depth allows the system to base modifications to the target depth on trends in physiological data that may have a slow response time. For example, feedback about the whether the rescuer is properly administering compressions at the target depth can be provided on a per compression time period while the information about whether the target depth should be modified could be analyzed and provided to the rescuer every 10-30 seconds (e.g., every 10 seconds, every 20 seconds, every 30 seconds).

Figure 14:
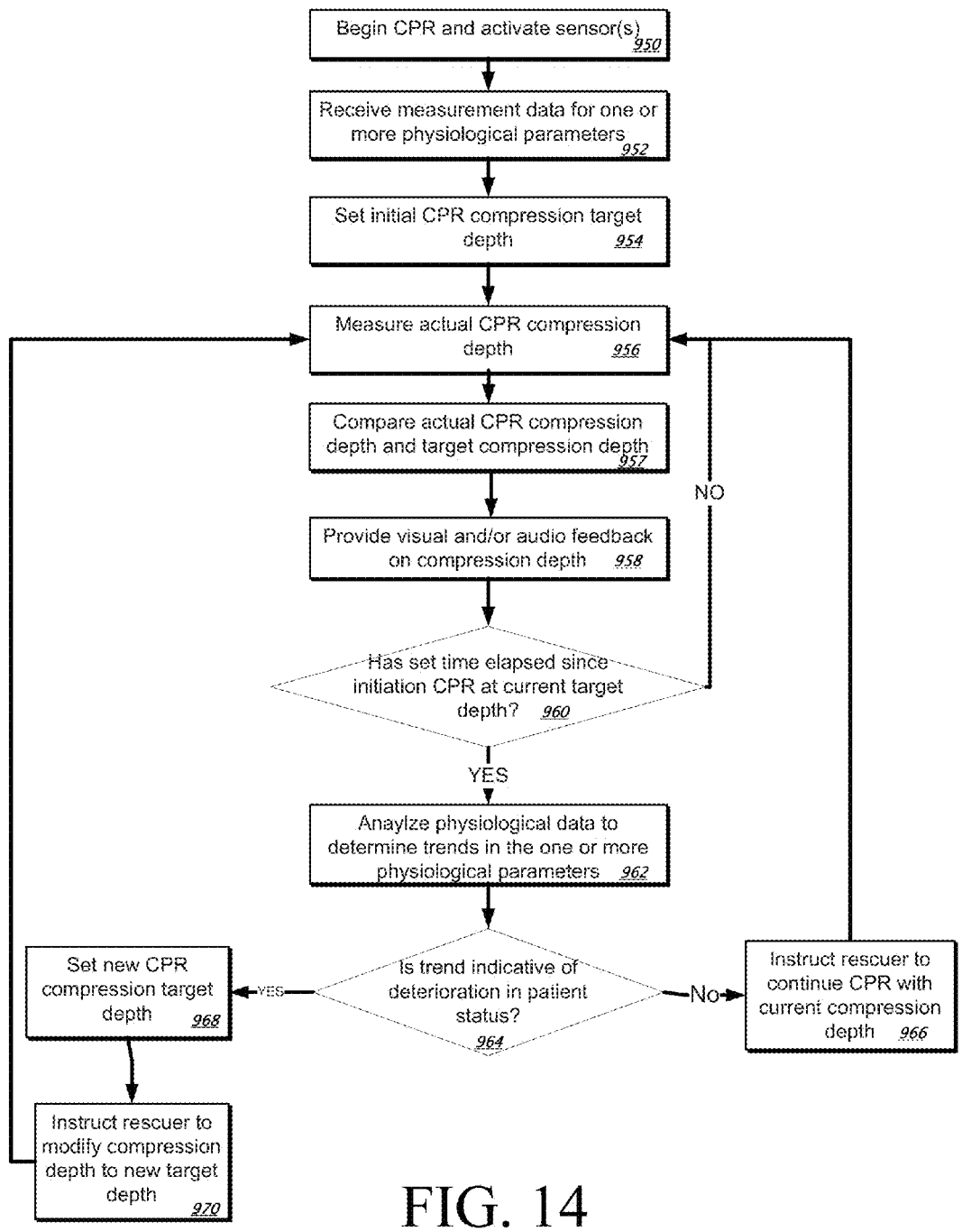
FIG. 14 is a flow chart showing actions taken to adjust a target compression depth and provide feedback on CPR quality to a rescuer.

FIG. 14 is a flowchart of a process for providing feedback to a rescuer who is administering manual CPR chest compressions to a victim. In general, the process involves deploying various medical devices at the scene of an emergency and providing feedback to the rescuer in relation to administration of CPR to the victim. The process is based on dual feedback loops which provide feedback related to whether the rescuer is properly administering chest compressions according to a rescue protocol and related to whether the rescue protocol (e.g., the target CPR compression depth) is appropriate.

Figure 1A:
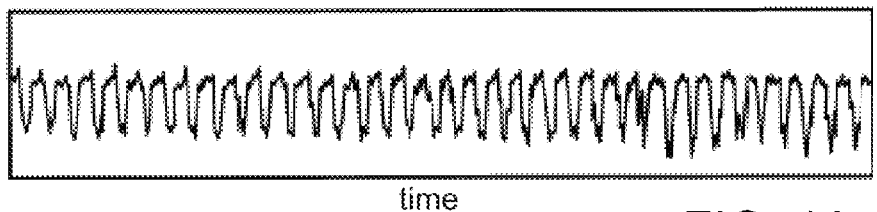
FIG. 1A is a magnitude versus time plot of a ventricular tachycardia (VT) rhythm.
Figure 1B:
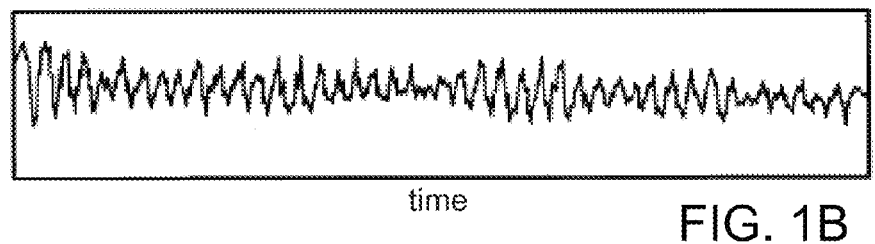
FIG. 1B is a magnitude versus time plot of a ventricular fibrillation (VF) rhythm.

The process begins at box 950, where the rescuer begins administration of manual CPR and various sensors are activated. A communication link is also established between the sensors and a feedback unit, which may be in the form of a tablet, like tablet 116 in FIG. 1, or a defibrillator like defibrillator 112 in FIG. 1. The communication may occur automatically upon activating the two communicating components, such as by instigating an automatic BLUETOOTH or WiFi connection in a familiar manner.

At box 952, measurement data for one or more physiological parameters is collected (e.g., using sensor devices described herein). Such information may be passed from the sensors to a computing component. Measurement data can include, for example, end-tidal $CO_2$ information from a capnometer, arterial pressure information from an arterial line in a radial artery of the victim.

At box 954, the system sets an initial compression target depth. The target depth can be selected based on the American Heart Association recommendations and/or based on other baseline recommendations for CPR. For example, the compression depth may be based on age, gender, and/or size of the victim. The compression target depth is used by the system to provide feedback to the rescuer regarding the quality of the administered CPR compressions.

At box 956, the system measures the actual CPR compression depth for CPR chest compressions administered by the rescuer. For example, a defibrillator or other device can include an accelerometer that is positioned to move in coordination with the patient's breastbone. Determining a value for depth can include double integrating measurements from the accelerometer. In some examples, the accelerometer can be attached to a housing that is in turn attached to a pair of defibrillator electrodes to be placed on the patient.

At box 957, the system compares the measured compression depths to the target compression depth and, at box 958, the system provides visual and/or audio feedback to the rescuer regarding the compression depth. For example, the system can generate an audio and/or visual prompt instructing the rescuer to press more deeply or less deeply, display a perfusion performance indicator (e.g., as described above), display a CPR Compression bar graph (e.g., as shown in FIG. 11), display a CPR depth meter (e.g., as shown in FIG. 12), and/or provide other indications of CPR compression depth.

At box 960, the system determines whether a set period of time has elapsed since initiation of CPR at the current target depth. The set period of time can be based on the average amount of time believed to be adequate to observe a change in a physiological parameter based on the CPR compressions. For example, the set period of time can be between 10 seconds and 1 minute (e.g., between 10 seconds and 30 seconds, between 10 seconds and 20 seconds, between 30 seconds and one minute, about 10 seconds, about 20 seconds, about 30 seconds). In one particular example, the system can measure arterial pressure and the set period of time can be about 45-60 seconds to allow a change to be observed in the arterial pressure before determining whether to modify the target compression depth. In another example, the system can measure end-tidal $CO_2$ and the set period of time can be about 10-20 seconds to allow a change to be observed in end-tidal $CO_2$ before determining whether to modify the target compression depth.

If the set period of time has not yet elapsed, the process returns to box 956 and continues to observe compression depth (box 956), compare the compression depth to the target depth (box 957), and provide feedback to the rescuer about the compression depth (box 958).

If the set period of time has elapsed, at box 962, the system performs calculations and/or comparisons to analyze the physiological data and determine trends in the measured physiological parameter(s). Alternatively, the system can compare measured values of the physiological parameter(s) to threshold values to determine a status of the victim.

At box 964, the system determines whether the trend (or the measured value) is indicative of deterioration of the patient's status. If not (e.g., if the victim is improving or remains stable), at box 966, the system instructs the rescuer to continue CPR using the current target CPR compression depth and returns to box 956. On the other hand, if the trend is indicative of patient deterioration, at box 968, the system sets a new CPR compression target depth. For example, the system can increase the target compression depth by a fraction of an inch as described herein. In the arterial pressure example above, the target compression depth could be increased if the arterial pressure is decreasing and/or if the arterial pressure is below about 50 mmHg. In the end-tidal $CO_2$ example above, the target compression depth could be increased if the end-tidal $CO_2$ is decreasing and/or if the end-tidal $CO_2$ is below about 15-20. At box 970, the system instructs the rescuer to modify the compression depth to provide compressions at the new, updated target compression depth. After instructing the user to modify the compression depth, the process returns to box 956 and continues to observe compression depth (box 956), compare the compression depth to the new, updated target depth (box 957), and provide feedback to the rescuer about the compression depth (box 958). In some examples, the target depth is adjusted only if the rescuer is achieving compressions with a depth close to the target depth. In such examples, the system would not adjust the target depth if the rescuer was not achieving the current target because the information received would not necessarily indicate that a higher target is optimal for the patient. Rather, the system could encourage the rescuer to achieve the current target which might improve physiological status.

In some exemplary implementations, the system can determine whether to adjust the target compression depth based on multiple factors including the physiological information and the quality of the CPR compressions. For example, some rescuers such as lay rescuers may have difficulty in accurately controlling the depth of the CPR compressions. If the rescuer is unable to maintain control over the CPR compression depth, making minor adjustments in the target compression depth may distract the rescuer and/or the rescuer might be incapable of providing control over the depth of the compressions to actually provide compressions at the new target depth. In some examples, if the variance in the CPR compression depth is too large (e.g., greater than 0.5 inches) or the absolute depth is too far from the target depth, the system may instruct the rescuer to focus on providing the current target compression depth and providing compressions of consistent depth rather than adjust the compression depth based on changes in physiological parameters. On the other hand, the system adjusts the target compression depth when the rescuer is providing CPR compressions within a particular variance from the target compression depth and the physiological measurements show that an increase in depth could be beneficial.

In some examples, it can be beneficial to provide visual feedback associated with the measured physiological parameter (e.g., the end-tidal $CO_2$ or the arterial pressure). The feedback associated with the measured physiological parameter can provide the rescuer with information about the victim and help the rescuer to determine whether the victim's status is improving or deteriorating. If the rescuer is a trained rescuer (e.g., an EMT or other medical personnel), the rescuer may modify the treatment of the victim based on trends observed in the physiological parameters. For example, the rescuer might increase compression depth if the end-tidal $CO_2$ or the arterial pressure is trending downward. Various forms of visual feedback can convey information about the measured physiological parameter.

Figure 15A:
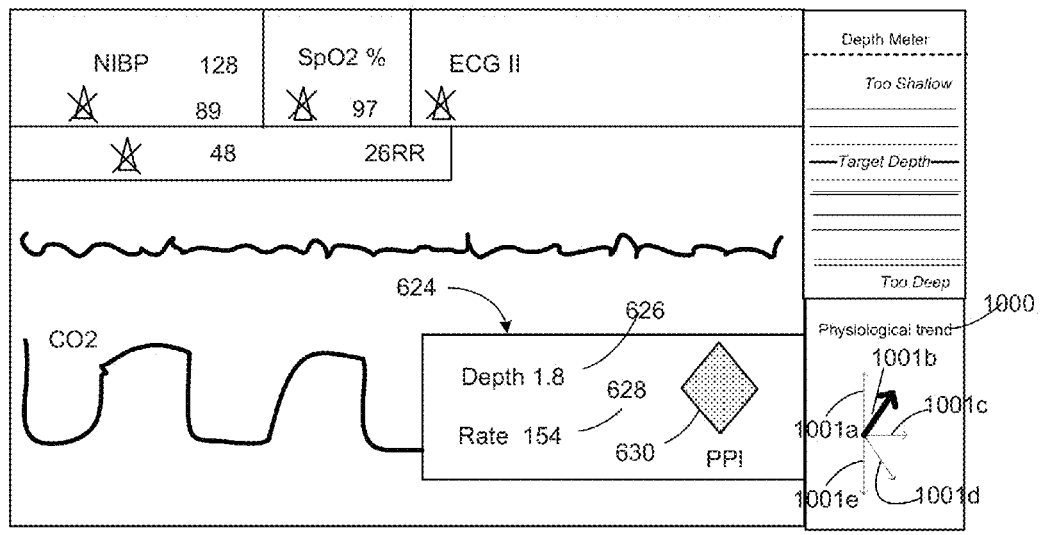
FIG. 15A is a screenshot showing exemplary information presented on a defibrillator display.

As shown in FIG. 15A, trend data 1000 can convey information about a measured physiological parameter. The trend data 1000 can include a set of trend arrows (e.g., arrows 1001a-e) in various orientations. The orientation of each arrow can convey the trend in the measured parameter. For example, arrow 1001a is pointed straight upward to show that the physiological parameter is sharply increasing, arrow 1001b is angled upward (e.g., at a 45 degree angle) to show that the physiological parameter is moderately increasing, arrow 1001c is pointed straight to the right to show that the physiological parameter is stable and not increasing or decreasing by an appreciable amount, arrow 1001d is angled downward (e.g., at a 45 degree angle) to show that the physiological parameter is moderately decreasing, and arrow 1001e is pointed straight downward to show that the physiological parameter is sharply decreasing. Visual indicia can differentiate the arrow associated with the current trend in the observed physiological data from the other arrows. In this example, arrow 1001b is shown in bold with a greater thickness than the other arrows. In another example, the arrow associated with the current trend could be shown in a different color. As such, a rescuer viewing the trend data 1000 can quickly assess whether the physiological parameter indicates improvement, stability, or a decline in the patient status and adjust treatment accordingly.

Figure 15B:
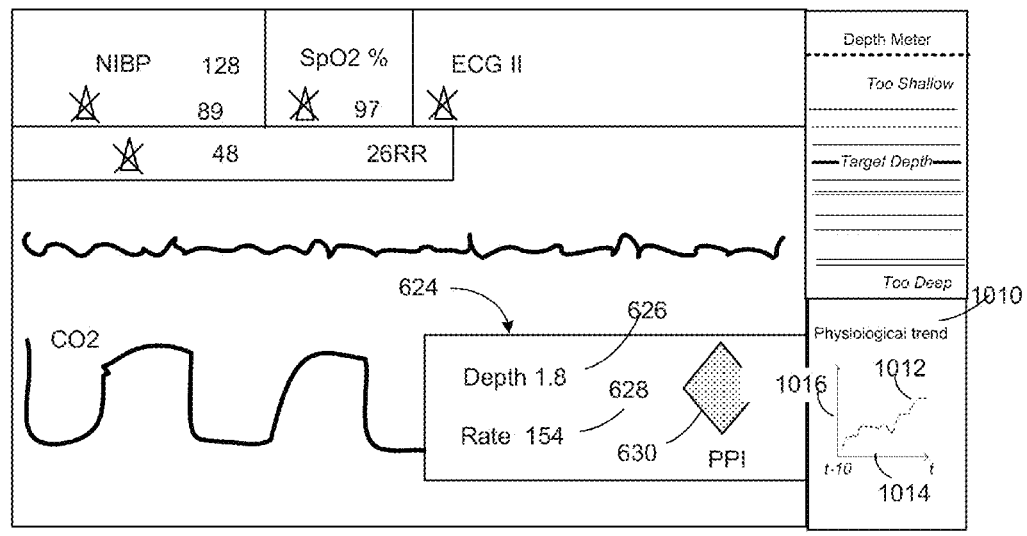
FIG. 15B is a screenshot showing exemplary information presented on a defibrillator display.

In another example, as shown in FIG. 15B, trend data 1010 can convey information about a measured physiological parameter as a graph 1012 of the physiological data. The trend data be plotted versus time (axis 1014) and display recent measurements. In the example shown in FIG. 15B, the most recent 10 seconds of measured data is displayed on the graph 1012. In some examples, in order to simplify the graph, the graph does not include the actual numeric value for the data (e.g., axis 1016 does not include values for the data). As such, a rescuer viewing the trend data 1010 can quickly assess whether the physiological parameter indicates improvement, stability, or a decline in the patient status and adjust treatment accordingly. In some examples, additional visual indicia can be provided on the trend data 1010 such as color coding of the graph 1012 based on a comparison of the trend data to a threshold. For example, if the value of the data or the trend in the data is associated with victim improvement, the graph could be displayed in green and if the value of the data or the trend in the data is associated with victim deterioration, the graph could be displayed in red.

While at least some of the embodiments described above describe techniques and displays used during manual human-delivered chest compressions, similar techniques and displays can be used with automated chest compression devices such as the AutoPulse device manufactured by ZOLL Medical, MA.

While at least some of the embodiments described above describe techniques and displays used in conjunction with an AED device, similar techniques and displays can be used with other defibrillator devices. Exemplary professional grade defibrillator devices include the R series, E series or M series devices manufactured by ZOLL Medical, MA and the Philips MRX or Philips XL devices.

Additionally, the defibrillator may take the form of a wearable defibrillator such as the LifeVest, manufactured by ZOLL Medical (Chelmsford, Mass.).

Many other implementations other than those described may be employed, and may be encompassed by the following claims.

What is claimed is:

1. A method for providing adaptive Cardiopulmonary Resuscitation (CPR) treatment to a person in need of emergency assistance, the method comprising:
   obtaining data representing chest compression depth from at least one sensor located on a chest of a person receiving CPR and arranged to move in conjunction with chest compressions performed by a user;
   providing, at a first rate, periodic feedback to the user about the chest compressions performed by the user based at least in part on data obtained from the at least one sensor and a target compression depth,
   periodically determining, at a second rate that is slower than the first rate, whether to adjust the target compression depth based at least in part on a trend represented in obtained information about a physiological parameter not based on an ECG signal of the person,
   upon determining to adjust the target compression depth, providing information to the user about an updated target compression depth and the obtained data representing chest compression depth.

2. The method of claim 1, wherein the periodic feedback to a user about the chest compressions performed by the user includes feedback about the compression depth.

3. The method of claim 1, wherein the trend is indicative of an effectiveness of the chest compressions and the target compression depth.

4. The method of claim 3, further comprising:
   calculating a derivative of the physiological information to determine the trend in the information.

5. The method of claim 1, wherein the trend in the information about the physiological parameter of the person is indicative of a lack of patient improvement.

6. The method of claim 1, further comprising:
   receiving information about the patient's heart activity.

7. The method of claim 6, wherein the patient heart activity is obtained by a portable computing unit that is integrated within a portable defibrillator.

8. The method of claim 6, further comprising:
   determining whether a shockable rhythm is likely to be present in the patient upon completion of CPR treatment based at least in part on the patient's heart activity; and
   upon determining the shockabable rhythm is likely to be present, charging the portable defibrillator such that the portable defibrillator is charged at the completion of the CPR treatment.

9. The method of claim 8, wherein the completion of the CPR treatment is determined based on a predetermined length of time for administering chest compressions.

10. The method of claim 8, wherein determining whether a shockable rhythm is likely to be present is based at least in part on at least one of the following data: ECG, pulse oximetry, capnography, respiration, and impedance cardiography.

11. The method of claim 8, wherein the portable defibrillator is charged to a level based at least in part on the information about the patient's heart activity.

12. The method of claim 11, wherein the level is determined at least in part on at least one of the following: an amplitude of an ECG signal, a frequency of an ECG signal, and an amplitude magnitude spectrum area value.

13. An external defibrillator, comprising:
   one or more sensors arranged to contact a patient and obtain measurements regarding chest compressions performed on the patient;
   one or more additional sensors arranged to contact a patient and obtain measurements regarding a physiological parameter not based on an ECG signal of the patient;
   feedback device configured to provide, at a first rate, periodic feedback to a user about chest compressions performed by the user based at least in part on the values for the depths of the chest compressions and a target compression depth; and
   a processor to execute instructions, stored in a memory, for:
   periodically determining, at a second rate that is slower than the first rate, whether to adjust the target compression depth based at least in part on a trend represented in the information about the physiological parameter not based on an ECG signal of the patient; and
   upon determining to adjust the target compression depth, providing information to the user about the updated target compression depth;
   wherein the feedback device is further configured to provide periodic feedback of the performed chest compressions based at least in part on the values representing the depths of the chest compressions and the updated target compression depth.

14. The external defibrillator of claim 13, wherein the physiological parameter not based on an ECG signal of the patient comprises at least one of carbon dioxide level, oxygen level, arterial pressure, blood pressure, and carotid blood flow.

15. The external defibrillator of claim 13, further comprising one or more batteries for powering the external defibrillator.

16. The external defibrillator of claim 15, wherein the processor further executes instructions for:
   determining whether a shockable rhythm is likely to be present at the end of a CPR interval; and
   upon determining that a shockable rhythm is likely to be present, charging the external defibrillator such that the external defibrillator is charged at the end of the CPR interval.

17. The external defibrillator of claim 16, wherein the processor further executes instructions for:
   charging the external defibrillator to a level based at least in part on the information about the patient's heart activity.

18. A system comprising:
   an external defibrillator;
   a feedback device configured to provide, at a first rate, periodic feedback to a user about chest compressions performed by the user based at least in part on obtained values for the depths of the chest compressions and a target compression depth; and
   a processor to execute instructions, stored in a memory, for:
   periodically determining, at a second rate that is slower than the first rate, whether to adjust the target compression depth based at least in part on a trend represented in obtained information about a physiological parameter not based on an ECG signal of a person; and
   upon determining to adjust the target compression depth, providing information to the user about an updated target compression depth,
   wherein the feedback device is further configured to provide periodic feedback of the performed chest compressions based at least in part on the values for the depths of the chest compressions and the updated target compression depth.

19. The system of claim 18, wherein the physiological parameter not based on an ECG signal of the person comprises at least one of carbon dioxide level, oxygen level, arterial pressure, blood pressure, and carotid blood flow.

20. The system of claim 18, further comprising one or more batteries for powering the external defibrillator.

21. The system of claim 20, wherein the processor further executes for:
 determining whether a shockable rhythm is likely to be present at the end of a CPR interval; and
 upon determining that a shockable rhythm is likely to be present, charging the external defibrillator such that the external defibrillator is charged at the end of the CPR interval.

22. The system of claim 21, wherein the processor further executes for:
 charging the external defibrillator to a level based at least in part on the information about the person's heart activity.

23. The method of claim 1, wherein the physiological parameter not based on an ECG signal of the person comprises at least one of carbon dioxide level, oxygen level, arterial pressure, blood pressure, and carotid blood flow.

* * * * *